(12) United States Patent
Jarvelainen et al.

(10) Patent No.: US 12,351,653 B1
(45) Date of Patent: *Jul. 8, 2025

(54) PHARMACEUTICAL COMPOSITIONS COMPRISING NOVEL CYCLIC PEPTIDES

(71) Applicant: LISATA THERAPEUTICS, INC., Basking Ridge, NJ (US)

(72) Inventors: Harri Jarvelainen, Tampere (FI); Erkki Ruoslahti, Rancho Santa Fe, CA (US)

(73) Assignee: LISATA THERAPEUTICS, INC.

( * ) Notice: Subject to any disclaimer, the term of this patent is extended or adjusted under 35 U.S.C. 154(b) by 0 days.

This patent is subject to a terminal disclaimer.

(21) Appl. No.: 19/023,048

(22) Filed: Jan. 15, 2025

Related U.S. Application Data

(63) Continuation-in-part of application No. 19/018,888, filed on Jan. 13, 2025, which is a continuation of application No. 17/737,008, filed on May 4, 2022, now abandoned, application No. 19/023,048, filed on Jan. 15, 2025 is a continuation-in-part of application No. 17/923,408, filed as application No. PCT/US2021/030740 on May 4, 2021, application No. 19/023,048, filed on Jan. 15, 2025 is a continuation-in-part of application No. 16/812,107, filed on Mar. 6, 2020.

(60) Provisional application No. 63/184,198, filed on May 4, 2021, provisional application No. 63/329,321, filed on Apr. 8, 2022, provisional application No. 63/019,799, filed on May 4, 2020, provisional application No. 62/815,917, filed on Mar. 8, 2019.

(51) Int. Cl.
*C07K 7/64* (2006.01)
*A61K 38/12* (2006.01)
*A61K 45/06* (2006.01)

(52) U.S. Cl.
CPC ............. *C07K 7/64* (2013.01); *A61K 38/12* (2013.01); *A61K 45/06* (2013.01)

(58) Field of Classification Search
None
See application file for complete search history.

(56) References Cited

U.S. PATENT DOCUMENTS

| 8,367,621 B2 | 2/2013 | Ruoslahti et al. |
| 9,073,974 B2 | 7/2015 | Lam et al. |
| 9,115,170 B2 | 8/2015 | Ruoslahti et al. |
| 9,694,074 B2 | 7/2017 | Cunin et al. |
| 10,370,245 B2 | 8/2019 | Ruoslahti et al. |
| 11,059,718 B2 | 7/2021 | Ruoslahti et al. |
| 11,260,133 B2 | 3/2022 | Ruoslahti et al. |
| 2009/0246133 A1 | 10/2009 | Ruoslahti et al. |
| 2010/0322862 A1 | 12/2010 | Ruoslahti et al. |
| 2013/0115628 A1 | 5/2013 | Isaacson et al. |
| 2015/0174263 A1 | 6/2015 | Sengupta et al. |
| 2015/0259380 A1 | 9/2015 | Ruoslahti et al. |
| 2017/0216402 A1 | 8/2017 | Wittrup et al. |
| 2018/0064662 A1 | 3/2018 | Fukumura et al. |
| 2020/0282013 A1 | 9/2020 | Jarvelainen et al. |
| 2022/0175941 A1 | 6/2022 | Ruoslahti et al. |
| 2023/0201303 A1 | 6/2023 | Ruoslahti et al. |

FOREIGN PATENT DOCUMENTS

| CN | 102600489 A | 7/2012 | |
| CN | 107892710 A | 4/2018 | |
| EP | 2445536 B1 * | 6/2016 | ............. A61K 47/50 |
| JP | 2014226079 A | 12/2014 | |
| JP | 2019501198 A | 1/2019 | |
| WO | 2000103718 A2 | 1/2001 | |
| WO | 2017120537 A1 | 7/2017 | |
| WO | 2017190684 A1 | 11/2017 | |
| WO | 2018089669 A2 | 5/2018 | |
| WO | 2018213631 A1 | 11/2018 | |

OTHER PUBLICATIONS

Jarvelainen et al. (Int. J. Mol. Sci. 2023, 24, 5700) (Year: 2023).*
Dean et al. (Lancet Gastroenterol Hepatol 2022; 7: 943-51) (Year: 2022).*
Liu et al. (Mol Syst Des Eng. Oct. 1, 2017; 2(4): 370-379) (Year: 2017).*
Pan et al. (Cell Rep Med. Jun. 18, 2024;5(6):101590) (Year: 2024).*
Akashi; Anticancer Effects of Gemcitabine are Enhanced by co-administered iRGD peptide in murine pancreatic cancer models that overespressed neuropilin-a; British Journal of Cancer, 2014-110, 1481-1487—7 pages.
Alva et al., Cancer Immunol Immunother. 2016; 65(12): 1533-1544).
Botta et al., "iRGD in Combination with IL-2 Reprograms Tumor Immunosuppression" NIH KL2TR002552, NCI. KYGF9753, SCMG Grant 90105000008254, SBP Grant 04032018; SBP Medical Discovery Institute, 1 page.
Cayrol et al. The IL-1-like cytokine I L-33 is inactivated after maturation by caspase-1. Proc Natl Acad Sci U SA. Jun. 2, 2009; 106(22 ): 9021-9026. (Year: 2009).
Charych et al (2016). NKTR-214, an Engineered Cytokine with Biased IL2 Receptor Binding, Increased Tumor Exposure, and Marked Efficacy in Mouse Tumor Models. Clin Cancer Res 22: 680-690.
Dean et al. 1528P Phase I trial of the first-in-class agent CEND-1 in combination with gemcitabine and nab-paclitaxel in patients with metastatic pancreatic cancer. Annals of Oncology. 2020;31 (4):S 934) (Year: 2020).

(Continued)

*Primary Examiner* — Sergio Coffa
(74) *Attorney, Agent, or Firm* — PROCOPIO, CORY, HARGREAVES & SAVITCH LLP

(57) ABSTRACT

Provided herein are novel cyclic peptides, their synthetic process, compositions, properties including stability and pharmacokinetic profiles, and applications for treating solid tumor cancers.

14 Claims, 6 Drawing Sheets

(56) References Cited

OTHER PUBLICATIONS

Dutcher, J. P. et al., High dose interleukin-2 (Aldesleukin)—expert consensus of best management practices—2014, Journal for Immunotherapy of Cancer, 2014, vol. 2, No. 1, 26, doi: 10.1186/s40425-014-0026-0.

Harada, K. et al., Long-term response to very-low-dose interleukin-2 therapy in patients with metastatic renal cell carcinoma; report of two cases, Clinical and Experimental Nephrology, 2011, vol. 15, No. 6, pp. 966 to 968, doi:10.1007/s10157-011-0518-x (newly cited publication).

Hurtado De Mendoza et al. "Tumor-penetrating therapy for 5 integrin-rich pancreas cancer," Nature.

ISR related to PCT/US2020/21570 dated Jun. 22, 2020.

International Search Report and Written Opinion for related PCT/US22/27735 dated Aug. 22, 2022, 9 pages.

Jarvelainen, H et al. Abstract 1 106: co-administration of the IRGD tumorpenetrating peptide.

Johnson et al. Nature Communications 17:10582, Melanoma-specific MHC-11 expression represents a tumour-autonomous phenotype and predicts response to anti-PD-1/PD-L 1 therapy (Year: 2015).

Lo, Jhj. "Targeting Nucleic Acids for Pancreatic Cancer: Disease Modeling and Therapy.". Doctoral Thesis (online). Massachusetts Institute of Technology. Retrieved From The Internet: [URL: Https:I//dspace.mit.edu/handle/1721.1/98574]. Sep. 17, 2015; Abstract; p. 4, Paragraph 2; p. 5, Paragraph 3; p. 21, Paragraph 2; p. 22, Paragraph 1; p. 48, Paragraph 2; p. 69, Paragraph 1; p. 73, Paragraph 3.

Marino et al., Protein Termini and Their Modifications Revealed by Positional Proteomics, ACS Chemical Biology, 2015, 1754-1764, 11 pages.

Medical news today by Christina Chun, https://www.medicalnewstoday.com/articles/322700 Accessed May, 8, 2020 (Year: 2018).

"Merck manual, cancer treatment principles, by Robert Gale, https://www.merckmanuals.com/home/cancer/prevention-and-treatment-of-cancer/cancer-treatment-pri nci ples?query=Cancer%2otreatment Accessed May 8, 2020 (Year: 2018)".

Merck manual, overview of cancer therapy, by Robert Gale, https://www.merckmanuals.com/professional/hematology-and-oncology/principles-of-cancer-therapy/overview-of-cancer-therapy?query=Cancer Accessed May 8, 2020 (Year: 2018).

National cancer institute, what is cancer? https://www.cancer.gov/about-cancer/understanding/what-is-cancer accessed on May 8, 2020 (Year: 2015).

National cancer institute, cancer prevention, https://www.cancer.gov/about-cancer/causes-prevention/ patient- prevention-overview-pdq accessed May 8, 2020 (Year: 2020).

PCT/IB/326 Form: International Preliminary Report on Patentability for PCT/US2021/03074.

Rosenberg; "Raising the Bar: The Curative Potential of Human Cancer Immunotherapy", Sci Transl Med. Mar. 28, 2012; 4(127): 127ps8. doi: 10.1126/scitranslmed.3003634.

Rosenzwajg et al., "Low dose interleukin-2 fosters a dose-dependent regulatory T cell tuned milieu in T1 D patients" J Autoimmun., Apr. 2015; 58:48-58.

Ruoslahti (2017). Tumor penetrating peptides for improved drug delivery. Adv Drug Deliv Rev. 110-111: 3-12.

Sausville et al. Contributions of Human Tumor Xenografts to Anticancer Drug Development. Cancer Res 2006; 66: (7). Apr. 1, 2006 (Year: 2006).

Schmithals et al., Improving Drug Penetrability with iRGD Leverages the Therapeutic Response to Sorafenib and Doxorubicin in Hepatocellular Carcinoma, Cancer Research—Therapeutics, Targets and Chemical Biology, 2015, pp. 3147-3154.

Zhong et al., Co-Administered or iRGD Enhances Tumor-Targeted Delivery and Anti-Tumor Effects of Paclitaxel-Loaded PLGA Nanoparticles For Colorectal Cancer Treatment, International Journal of Nanomedicine; 18 pages, 2019.

Sugahara et al. Co-administration of a Tumor-Penetrating Peptide Enhances the Efficacy of Cancer Drugs. Science. May 21, 2010; 328(5981): 1031-1035 (Year: 2010).

Waldmann (2015). The shared and contrasting roles of interleukin-2 (IL-2) and IL-15 in the life and death of normal and neoplastic lymphocytes: implications for cancer therapy. Cancer Immunol Res. 3: 219-227.

Walker et al., Using protein-based motifs to stabilize peptides, J. Peptide Res., 2003, 62, 214-226.

Yang Jie et al: "Modification of IL-24 by 1-6,8-14 tumor penetrating peptide iRGD enhanced its antitumor efficacy Feb. 22, 2019), pp. 125-134, XP085646038_ 3 ligainst non-small cell lung cancer", International Immunopharmacology, vol. 70, Feb. 22, 2019.

Zeng et al. N-Terminal Acetylation and C-Terminal Amidation of Spirulina platensis-Derived Hexapeptide: Anti-Photoaging Activity and Proteomic Analysis. Mar. Drugs. 2019, 17, 520. (Year: 2019).

Botta et al.; iRGD in combination with IL-2 reprograms tumor immunosuppression; Journal of Clinical Oncology; 2019, 3 pages.

Botta et al.; Digital Program: 2019 ASCO-SITC Clinical Immuno-Oncology Symposium; Feb. 28-Mar. 2, 2019; ASCO Meeting Library, 3 pages.

CEND-1 Injection (QLC12102) in Patients With Advanced Metastatic Pancreatic Ductal Adenocarcinoma; ClinicalTrials.gov ID NCT05052567, Sponsor Qilu Pharmaceutical Co., Ltd., Last Update Posted Sep. 4, 2024; https://clinicaltrials.gov/study/NCT05052567?term=CEND-1&rank=1.

CEND-1 in Combination With Nabpaclitaxel and Gemcitabine in Metastatic Pancreatic Cancer, ClinicalTrials.gov ID NCT03517176, Sponsor Lisata Therapeutics, Inc., Information provided by Lisata Therapeutics, Inc. (Responsible Party), Last Update Posted Aug. 28, 2024, https://clinicaltrials.gov/study/NCT03517176?term=CEND-1&rank=2.

A Study of CEND-1 With Chemotherapy as First-Line Therapy in Patients With Pancreatic Ductal Adenocarcinoma, ClinicalTrials.gov ID NCT06261359, Sponsor Qilu Pharmaceutical Co., Ltd., Information provided by Qilu Pharmaceutical Co., Ltd. (Responsible Party), Last Update Posted Sep. 4, 2024, https://clinicaltrials.gov/study/NCT06261359?term=CEND-1&rank=3.

CEND-1 in Combination with Neoadjuvant FOLFIRINOX with or Without Panitumumab (CENDIFOX), ClinicalTrials.gov ID NCT05121038, Sponsor Anup Kasi, Information provided by Anup Kasi, University of Kansas Medical Center (Responsible Party), Last Update Posted Dec. 17, 2024, https://clinicaltrials.gov/study/NCT05121038?term=CEND-1&rank=4.

LSTA1 Phase 1b/☐2a Continuous Infusion Trial in mPDAC (Fortifide), ClinicalTrials.gov ID NCT06592664, Sponsor Lisata Therapeutics, Inc., Information provided by Lisata Therapeutics, Inc. (Responsible Party), Last Update Posted Dec. 13, 2024, https://clinicaltrials.gov/study/NCT06592664?term=CEND-1&rank=5.

The ASCEND Study: Gemcitabine and Nab-Paclitaxel With LSTA1 (Certepetide) or Placebo in Patients With Untreated Metastatic Pancreatic Ductal Adenocarcinoma (ASCEND), ClinicalTrials.gov ID NCT05042128, Sponsor Australasian Gastro-Intestinal Trials Group, Information provided by Australasian Gastro-Intestinal Trials Group (Responsible Party), Last Update Posted Oct. 22, 2024, https://clinicaltrials.gov/study/NCT05042128?term=CEND-1&rank=6.

A Study of LSTA1 When Added to Standard of Care Versus Standard of Care Alone in Patients With Advanced Solid Tumors (BOLSTER), ClinicalTrials.gov ID NCT05712356, Sponsor Lisata Therapeutics, Inc., Information provided by Lisata Therapeutics, Inc. (Responsible Party), Last Update Posted Mar. 14, 2025, https://clinicaltrials.gov/study/NCT05712356?term=CEND-1&rank=7.

* cited by examiner

PHARMACEUTICAL COMPOSITIONS COMPRISING NOVEL CYCLIC PEPTIDES

CROSS-REFERENCE TO RELATED APPLICATIONS

This application is a continuation-in-part of U.S. patent application Ser. No. 19/018,888, filed Jan. 13, 2025, which is a continuation of Ser. No. 17/737,008, filed on May 4, 2022, now abandoned, which claims the benefit of U.S. Provisional Pat. App. Nos. 63/184,198, filed May 4, 2021, and 63/329,321, filed Apr. 8, 2022; this application is also a continuation-in-part of U.S. patent application Ser. No. 17/923,408, filed Nov. 4, 2022, which is a national stage entry of International Pat. App. No. PCT/US2021/030740, filed May 4, 2021, which claims the benefit of U.S. Provisional Pat. App. No. 63/019,799, filed May 4, 2020; and this application is also a continuation-in-part of U.S. patent application Ser. No. 16/812,107, filed Mar. 6, 2020, which claims the benefit of U.S. Provisional Pat. App. No. 62/815,917, filed Mar. 8, 2019.

FIELD

The invention relates to compounds, methods and medicaments useful for treating disease, e.g., solid tumors.

BACKGROUND

The National Cancer Institute estimates that in 2018 approximately 1,735,350 new cases of cancer will be diagnosed in the United States and 609,640 people will die from the disease. Despite advances in the treatment of certain forms of cancer through surgery, radiotherapy, chemotherapy, and most recently immunotherapy, most types of solid tumors are essentially incurable. Even when an effective treatment is available for a particular cancer, the side effects from the treatment can have a significant adverse impact on a patient's quality of life.

Pancreatic cancer is an especially serious cancer and a life-threatening condition. In most cases, early stages of the disease are asymptomatic and less than 20% of pancreatic cancers are amenable to surgery. Moreover, invasive and metastatic pancreatic cancers respond poorly to existing treatments in chemotherapy and radiotherapy, with response rates typically less than 30%. The National Cancer Institute (NCI) estimate that survival rate for cancer of the exocrine pancreas is less than 5% and the median survival time after diagnosis is less than a year. The continuing poor prognosis and lack of effective treatments for pancreatic cancer highlight an unmet medical need to develop less toxic and more efficient treatment strategies that improve the clinical management and prognosis of patients afflicted with pancreatic cancer.

An important reason for why most anti-cancer agents have toxicity and limited efficacy for solid tumors is the fact that anti-cancer drugs only penetrate 3-5 cell diameters deep from the blood vessels, leaving some areas of the tumor exposed to an ineffective concentration of the drug or to no drug at all. As an example, studies have suggested that less than 1% of the administered nabpaclitaxel may be able to penetrate/enter the pancreatic ductal adenocarcinoma tissue.

SUMMARY

Improved Penetration of Chemotherapeutics with CEND-1

The results from both in vivo and in vitro pharmacology and mechanistic studies indicate that combining the invention CEND-1 (FIG. 2), an iRGD-analog, with chemotherapeutics significantly increases the tumor penetration of these drugs and improves their efficacy. Although the invention methods are applicable to a broad class of cancers and/or solid tumors, the initial indication for this investigational drug is pancreatic ductal adenocarcinoma (PDAC) because, in addition to its poor prognosis, it is characterized by a dense extracellular matrix stroma, which acts as a physical barrier to drug entry. Since the tumor homing and the transport process initiated by CEND-1 have been shown to be active in the PDAC stroma and preclinical studies have shown increased drug penetration and efficacy in different kinds of PDAC models, CEND-1 appears particularly well suited to target PDAC.

Accordingly, provided herein are pharmaceutical composition comprising: an iRGD-analog and a pharmaceutically acceptable excipient. In a particular embodiment, the invention composition corresponds to the iRGD-analog set forth as the structure in FIG. 2 (i.e., CEND-1). The invention CEND-1 differs from the prior art iRGD peptides in the specific moieties used to block the amino and carboxy termini, which has resulted in significant advantages over prior art cyclic iRGD peptides. For example, the invention iRGD-analog (set forth in FIG. 2 as CEND-1) has the following molecular formula C37 H60 N14 O14 S2; a MW 989.1; and the recent CAS Registry #: 2580154-02-3. Whereas one prior art iRGD with at least one inferior therapeutic property corresponds to an iRGD having the Molecular Formula: $C_{35}H_7N13O14_4S2$; a Molecular Weight of 948.04; and CAS Registry No. 1392278-76-0.

Advantages of the invention CEND-1 iRGD-analog (FIG. 2; C37 H60 N14 O14 S2; MW 989.1), relative to prior art CAS Registry No. 1392278-76-0 cyclic peptide and other known iRGD molecules, while maintaining favorable in vitro/in vivo potency and efficacy include one or more of the following:

Favorable pharmacokinetic properties;
Improved stability in plasma/serum (e.g., Pooled human plasma, as set forth in the Examples herein);
Improved stability in formulated solution;
Improved stability in storage (e.g., phosphate buffered saline, as set forth in the Examples herein); and/or
Improved protection from proteases such as aminopeptidases and carboxypeptidases.

In certain embodiments, favorable and/or improved pharmacokinetic properties are selected from one or more of absorption, distribution, metabolism, and/or excretion. In particular embodiments, CEND-1 has a degradation rate 3-fold lower (e.g., improved stability) than the degradation rate of iRGD in phosphate buffered saline, 37° C. and pH=7.4; and/or a degradation rate 1.6-fold lower than the degradation rate of iRGD in in pooled human plasma. In another embodiment, CEND-1 has been found to have a 46% increased half-life compared to iRGD in vivo.

Provided herein are methods for treating, inhibiting, or reducing the volume of a tumor of a cancer in a subject or patient in need thereof, wherein the method comprises administering CEND-1, or a pharmaceutically acceptable salt thereof, in a combination with simultaneous, separate or sequential administration of at least one anti-cancer agent or therapy. In certain embodiments, the tumor is a malignant solid tumor characterized by dense tumor stroma. In other embodiments, the tumor is a solid tumor of a cancer selected from the group consisting of: breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma, and head and neck cancer. In another embodiment, the pancreatic cancer is selected from the group consisting of: primary pancreatic cancer, metastatic pancreatic cancer, refractory pancreatic cancer, cancer drug resistant pancreatic cancer and adenocarcinoma. In a particular embodiment, the cancer is ductal adenocarcinoma, such as Stage 0-IV, and the like.

In particular embodiments, the anti-cancer agent or therapy is selected from the group consisting of: a chemotherapeutic agent, small molecule, antibody, antibody drug conjugate, nanoparticle, cell therapy, polypeptides, peptides, peptidomimetics, nucleic acid-molecules, ribozymes, antisense oligonucleotides, and nucleic acid molecules encoding transgenes, viruses, cytokines, cytotoxic polypeptides; pro-apoptotic polypeptides, anti-angiogenic polypeptides, cytotoxic cells such as cytotoxic T cells, and/or vaccines (mRNA or DNA).

In other embodiments, the chemotherapeutic agent is selected from one or more of the group consisting of: taxane, docetaxel, paclitaxel, nab-paclitaxel, a nucleoside, gemcitabine, an anthracycline, doxorubicin, an alkylating agent, a vinca alkaloid, an anti-metabolite, a platinum agent, cisplatin, carboplatin, a steroid, methotrexate, an antibiotic, adriamycin, an isofamide, a selective estrogen receptor modulator, a maytansinoid, mertansine, emtansine, an antibody such, trastuzumab, an anti-epidermal growth factor receptor 2 (HER2) antibody, trastuzumab, a caspase, caspase-8; diphtheria toxin A chain, *Pseudomonas* exotoxin A, cholera toxin, ligand fusion toxins, DAB389EGF, *Ricinus communis* toxin (ricin); chimeric antigen receptor T cells (CAR-T), chimeric antigen receptor macrophages (CAR-M), chimeric antigen receptor natural killer cells (CAR-K), and tumor-infiltrating lymphocytes (TIL), anti-PD-1 antibodies, nivolumab, panitumumab, pembrolizumab, atezolizumab, avelumab, durvalumab; anti-CTLA-4 antibodies. ipilimumab; bispecific antibodies, catumaxomab, Moderna's mRNA-4157 and/or BioNTech's BNT122.

In particular embodiments, CEND-1 (the iRGD-analog set forth in FIG. 2) is administered in an amount selected from the group consisting of: about 0.2 to 20 mg/kg body weight/per dose of cancer therapy, about 0.3 to 17 mg/kg body weight/per dose of cancer therapy, about 0.4 to 14 mg/kg body weight/per dose of cancer therapy, about 0.5 to 11 mg/kg body weight/per dose of cancer therapy, about 0.6 to 8 mg/kg body weight/per dose of cancer therapy, about 0.7 to 5 mg/kg body weight/per dose of cancer therapy, about 0.8 to 3.2 mg/kg body weight/per dose of cancer therapy. In a particular embodiment, CEND-1 is administered in an amount corresponding to 3.2 mg/kg body weight/per dose of cancer therapy.

In certain embodiments, CEND-1 is administered before or during the administration of anti-cancer therapy, wherein the cancer therapy is at a dosing regimen selected from the group consisting of: 4 times/day, 3 times/day, twice daily, once daily, once every other day, once every 2nd day, once every 3rd day, once every 4th day, once every 5th day, once every 6th day, once weekly, once every 8th day, once every 9th day, once every 10th day, once every 11th day, once every 12th day, once every 13th day, once every 2 weeks, once every 3 weeks, and/or once per month. In one embodiment, CEND-1 is present in a dry formulation or suspended in a biocompatible medium.

In particular embodiments, the biocompatible media is selected from the group consisting of: water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, and lipid-containing emulsions. In a particular embodiment, CEND-1 is administered intravenously.

Also provided herein is a method of treating pancreatic cancer in a patient in need thereof, comprising administering to the patient an effective amount of CEND-1, in combination with gemcitabine and/or nab-paclitaxel, or pharmaceutically acceptable salts thereof. In certain embodiments, the pancreatic cancer is selected from the group consisting of: primary pancreatic cancer, metastatic pancreatic cancer, refractory pancreatic cancer, cancer drug resistant pancreatic cancer and adenocarcinoma. In a particular embodiment, the cancer is ductal adenocarcinoma (Stage 0-IV).

In certain embodiments, CEND-1 is administered in an amount selected from the group consisting of: about 0.2 to 20 mg/kg body weight/per dose of cancer therapy, about 0.3 to 17 mg/kg body weight/per dose of cancer therapy, about 0.4 to 14 mg/kg body weight/per dose of cancer therapy, about 0.5 to 11 mg/kg body weight/per dose of cancer therapy, about 0.6 to 8 mg/kg body weight/per dose of cancer therapy, about 0.7 to 5 mg/kg body weight/per dose of cancer therapy, about 0.8 to 3.2 mg/kg body weight/per dose of cancer therapy. In once embodiment, CEND-1 is administered in an amount corresponding to 3.2 mg/kg body weight/per dose of cancer therapy.

In particular embodiments, CEND-1 is administered before or during the administration of anti-cancer therapy, wherein the cancer therapy is at a dosing regimen selected from the group consisting of: 4 times/day, 3 times/day, twice daily, once daily, once every other day, once every 2nd day, once every 3rd day, once every 4th day, once every 5th day, once every 6th day, once weekly, once every 8th day, once every 9th day, once every 10th day, once every 11th day, once every 12th day, once every 13th day, once every 2 weeks, once every 3 weeks, and/or once per month. In a particular embodiment of anti-cancer therapy, CEND-1 is administered in a range amount selected from: 0.01-100, 0.02-90, 0.03-80, 0.04-70, 0.05-60, 0.06-50, 0.07-40, 0.08-30, 0.09-30, 0.1-25, 0.11-20, 0.12-15, 0.13-10, 0.14-9, 0.15-8, 0.16-7, 0.17-6, 0.18-5, 0.19-4, or 0.2-3.2 mg/kg body weight/day or per dose of chemotherapy; nab-paclitaxel is administered in a range amount selected from: 1-500, 10-450, 20-400, 30-350, 40-300, 50-250, 60-200, 70-175, 80-160, 90-150, 100-140, 110-140, 115-135 or 120-130 mg/m2; and gemcitabine is administered in a range amount selected from: 1-5000, 100-4500, 200-4000, 300-3500, 400-3000, 500-2500, 550-2000, 600-1750, 650-1500, 700-1400, 750-1300, 800-1200, or 900-1100 mg/m2.

In yet another embodiment of anti-cancer therapy, CEND-1 is administered in a range of 0.2-3.2 mg/kg body weight/day or per dose of chemotherapy; nab-paclitaxel is administered at 125 mg/m2; and/or gemcitabine is administered at 1000 mg/m2. In yet a furtherer embodiment of anti-cancer therapy, CEND-1 is administered in a range of 0.2-3.2 mg/kg body weight/day or per dose of chemotherapy; nab-paclitaxel is administered at 125 mg/m2; and gemcitabine is administered at 1000 mg/m2.

In yet another embodiment of anti-cancer therapy, such as thyroid cancer, melanoma, liver cancer, e.g., hepatocellular carcinoma, renal cell carcinoma, and the like, the invention iRGD-analog CEND-1 is administered in a range amount selected from: 0.01-100, 0.02-90, 0.03-80, 0.04-70, 0.05-60, 0.06-50, 0.07-40, 0.08-30, 0.09-30, 0.1-25, 0.11-20, 0.12-15, 0.13-10, 0.14-9, 0.15-8, 0.16-7, 0.17-6, 0.18-5, 0.19-4, or 0.2-3.2 mg/kg body weight/day or per dose of chemotherapy, in combination with;

sorafenib is administered in a range amount selected from: 1-500, 10-450, 20-400, 30-350, 40-300, 50-250, 60-200, 70-175, 80-160, 90-150, 100-140, 110-140, 115-135 or 120-130 mg/m2; or: 100-1000 mg PO q12 hr, 200-800 mg PO q12 hr, 300-7000 mg PO q12 hr or 400 mg PO q12 hr; and/or doxorubicin is administered in a range amount selected from: 1-5000, 100-4500, 200-4000, 300-3500, 400-3000, 500-2500, 550-2000, 600-1750, 650-1500, 700-1400, 750-1300, 800-1200, or 900-1100 mg/m2.

In certain embodiments of the invention methods provided herein, efficacy or clinical activity of the method is measured by determining: Overall Response Rate (ORR), Progression Free Survival (PFS) and/or Overall Survival (OS). In yet further embodiments, efficacy or clinical activity of the method is measured by determining one or more of: an Overall Response Rate (ORR) selected from greater than 25%, 30%, 35%, 40%, 45%, 50%, 55%, 60%, 65%, 70%, 75%, 80%, 85%, 90%, or greater that 95%; a Progression Free Survival (PFS) selected from greater than 25%, 30%, 35%, 40%, 45%, 50%, 55%, 60%, 65%, 70%, 75%, 80%, 85%, 90%, or greater that 95%; and/or an Overall Survival (OS) selected from greater than 25%, 30%, 35%, 40%, 45%, 50%, 55%, 60%, 65%, 70%, 75%, 80%, 85%, 90%, or greater that 95%.

Also provided herein is a kit or composition comprising an iRGD-analog (CEND-1); and an anti-cancer agent. In a particular embodiment, the iRGD-analog is set forth as the structure in FIG. 2.

DETAILED DESCRIPTION

Figure 2:
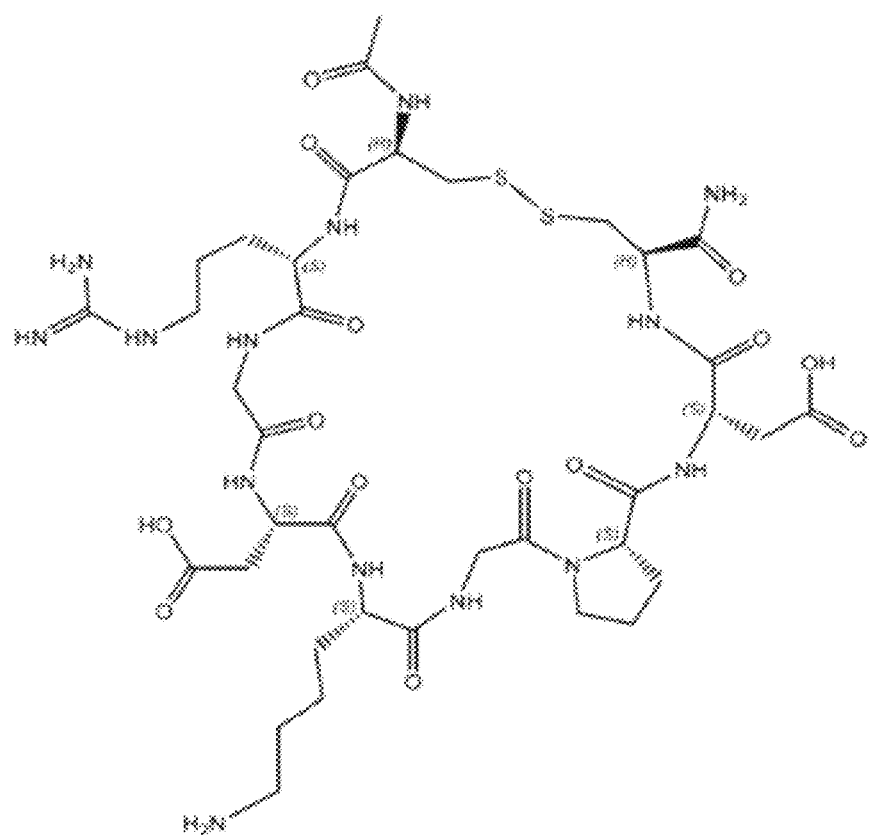
FIG. 2 shows the chemical structure of the invention CEND-1 iRGD-analog cyclic peptide having the molecular formula C37 H60 N14 O14 S2; a MW of 989.1; and the CAS Registry #: 2580154-02-3. It has all natural amino acids and can also be represented as follows: Ac-Cys-Arg-Gly-Asp-Lys-Gly-Pro-Asp-Cys-NH2 (Cys & Cys Bridge). It can also be represented as follows: L-cysteinyl-L-arginylglycyl-L-.alpha.-aspartyl-L-lysylglycyl-L-prolyl-L-.alpha.-aspartyl-L-cysteinyl, cyclic (1.fwdarw.9)-disulfide, with N-terminal amino group blocked by an acetyl group and the C-terminal carbonyl group by a carboxyamide group.

Provided herein are methods for treating, inhibiting, or reducing the volume of a tumor of a cancer in a subject or patient in need thereof, wherein the method comprises administering CEND-1, or a pharmaceutically acceptable salt thereof, in a combination with simultaneous, separate or sequential administration of at least one anti-cancer agent or therapy. The invention provides improved methods and medicaments for more effectively treating solid tumors with anti-cancer therapies. CEND-1 is a tumor-penetrating peptide that is an analog of iRGD (internalizing arginylglycylaspartic acid cyclic peptide). iRGD molecules in general, and CEND-1 in particular as an iRGD-analog, have a cyclizing (S—S bond through the cysteine side chains) structure containing nine amino acids. In a particular embodiment, an invention iRGD-analog corresponds to the invention iRGD-analog peptide sequence corresponding to the specific cyclic peptide chemical structure set forth in FIG. 2, i.e., CEND-1, set forth as Ac-Cys-Arg-Gly-Asp-Lys-Gly-Pro-Asp-Cys-NH2 and having CAS Registry #2580154-02-3. The pharmacological effect of CEND-1 is restricted to tumors via the primary RGD tumor homing motif interaction with αv-integrins (highly expressed in growing tumors but not in healthy tissues). The secondary 'CendR'—motif modulates the tumor microenvironment via NRP-1. Based on experimental models, the interaction with neuropilin-1 leads to transformation of the solid tumor microenvironment into a temporary drug conduit, allowing an efficient tumor access of anti-cancer therapies given in combination with CEND-1. Studies have demonstrated that CEND-1 increases, via the above-mentioned tumor microenvironment modulation mechanism, accumulation and penetration of anticancer drugs into tumors, but not into normal tissues. As a result, anti-tumor activity is enhanced, while the therapeutic margins/safety profile is potentially improved. In addition to the invention iRGD-analog (CEND-1; FIG. 2); other iRGD peptides and analogs known in the art, such as those described hereinabove, can be used in the invention methods, in view of the data, dosages and results provided herein.

In certain embodiments, the tumor is a malignant solid tumor characterized by dense tumor stroma. In other embodiments, the tumor is a solid tumor of a cancer selected from the group consisting of: breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma, and head and neck cancer. In another embodiment, the pancreatic cancer is selected from the group consisting of: primary pancreatic cancer, metastatic pancreatic cancer, refractory pancreatic cancer, cancer drug resistant pancreatic cancer and adenocarcinoma. In a particular embodiment, the cancer is ductal adenocarcinoma (such as Stage 0-IV, and the like.

As used herein the phrase "solid tumor" refers to essentially solid neoplasmic growth, with low liquid content that is other than a cyst or tumor metastasis (i.e. at its metastatic stage of disease).

As used herein, the phrase "in a combination" refers to administering more that one therapeutic agent to a respective patient in need thereof. In particular embodiments, CEND-1 is administered with at least one other anti-cancer therapeutic agent.

As used herein, the phrase "simultaneous, separate or sequential administration" refers to administering CEND-1 at the same time as the one or more other cancer therapeutic agents; or either before or after administration with the co-administered anti-cancer agents; such that the co-administration can be from separate pharmaceutical compositions administered with either the same or different dosing regimens. In certain embodiments, CEND-1 is administered before the subsequent and sequential administration of the one or more anti-cancer agents.

As used herein, the term "malignant" refers to a tumor or cancer in which abnormal cells divide without control and can invade nearby tissues. Malignant cancer cells can also spread to other parts of the body through the blood and lymph systems.

Based on the novel drug conduit mechanism discovered by the present inventors, the methods and medicaments of the present invention are suitable for using CEND-1 (an iRGD-analog) to enhance the therapeutic effects of any anticancer agent used to treat solid tumors. The methods and medicaments of the present invention can thus contain combinations of an iRGD-analog (CEND-1) with any anticancer agent used to treat solid tumors, such as at least one of a taxane such as docetaxel or paclitaxel (including nab-paclitaxel), a nucleoside such as gemcitabine, an anthracyclin such as doxorubicin, an alkylating agent, a vinca alkaloid, an anti-metabolite, a platinum agent such as cisplatin or carboplatin, a steroid such as methotrexate, an antibiotic such as adriamycin, an isofamide, a selective estrogen receptor modulator, or an antibody such as trastuzumab.

An anticancer agent whose effects can be enhanced by CEND-1 can be an antibody such as a humanized monoclonal antibody. As an example, the anti-epidermal growth factor receptor 2 (HER2) antibody, trastuzumab (Herceptin: Genentech, South San Francisco, Calif.) is a therapeutic agent useful in a conjugate for treating HER2/neu overexpressing breast cancers (White et al., Annu. Rev. Med. 52:125-141 (2001)).

Anticancer agents whose effects can be enhanced by CEND-1 also can be cytotoxic agents, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab, antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *Ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coro nado-Heinsohn, Cancer J. Sci. Am. 2: 175 (1996). One skilled in the art understands that these and additional cytotoxic agents described herein or known in the art can be combined with CEND-1 in the disclosed methods and medicaments.

In one embodiment, an anticancer agent whose effects can be enhanced by CEND-1 can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. An anticancer agent whose effects can be enhanced by CEND-1 can be an anti-angiogenic agent. As used herein, the term "anti-angiogenic agent" means a molecule that reduces or prevents angiogenesis, which is the growth and development of blood vessels. The combination of CEND-1 with anti-angiogenic agents can be used to treat cancer associated with angiogenesis.

A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and anti gen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

In particular embodiments, the anti-cancer agent or therapy is selected from the group consisting of: a chemotherapeutic agent, small molecule, antibody, antibody drug conjugate, nanoparticle, cell therapy, polypeptides, peptides, peptidomimetics, nucleic acid-molecules, ribozymes, antisense oligonucleotides, and nucleic acid molecules encoding transgenes, viruses, cytokines, cytotoxic polypeptides; pro-apoptotic polypeptides, anti-angiogenic polypeptides, cytotoxic cells such as cytotoxic T cells, and/or vaccines (mRNA or DNA).

In other embodiments, the chemotherapeutic agent is selected from one or more of the group consisting of: taxane, docetaxel, paclitaxel, nab-paclitaxel, a nucleoside, gemcitabine, an anthracycline, doxorubicin, an alkylating agent, a vinca alkaloid, an anti-metabolite, a platinum agent, cisplatin, carboplatin, a steroid, methotrexate, an antibiotic, adriamycin, an isofamide, a selective estrogen receptor modulator, a maytansinoid, mertansine, emtansine, an auristatin, monomethyl auristatin E (MMAE) and F (MMAF), a natural antimitotic drug, an antibody, trastuzumab, an anti-epidermal growth factor receptor 2 (HER2) antibody, trastuzumab, a caspase, caspase-8; diphtheria toxin A chain, *Pseudomonas* exotoxin A, cholera toxin, ligand fusion toxins, DAB389EGF, *Ricinus communis* toxin (ricin); chimeric antigen receptor T cells (CAR-T), chimeric antigen receptor macrophages (CAR-M), chimeric antigen receptor natural killer cells (CAR-K), and tumor-infiltrating lymphocytes (TIL), anti-PD-1 antibodies, nivolumab, panitumumab, pembrolizumab, atezolizumab, avelumab, durvalumab; anti-CTLA-4 antibodies. ipilimumab; bispecific antibodies, catumaxomab, anti-CD47 antibodies, enfortumab, sacituzumab, antibody-drug conjugates. Moderna's mRNA-4157 and/or BioNTech's BNT122.

In particular embodiments, CEND-1 (the iRGD-analog set forth in FIG. 2) is administered in an amount selected from the group consisting of: about 0.2 to 20 mg/kg body weight/per dose of cancer therapy, about 0.3 to 17 mg/kg body weight/per dose of cancer therapy, about 0.4 to 14 mg/kg body weight/per dose of cancer therapy, about 0.5 to 11 mg/kg body weight/per dose of cancer therapy, about 0.6 to 8 mg/kg body weight/per dose of cancer therapy, about 0.7 to 5 mg/kg body weight/per dose of cancer therapy, about 0.8 to 3.2 mg/kg body weight/per dose of cancer therapy. In a particular embodiment, CEND-1 is administered in an amount corresponding to 3.2 mg/kg body weight/per dose of cancer therapy.

As used herein, the phrase "per dose of cancer therapy" refers to the co-administration of CEND-1 with one or more anti-cancer agents, such that each time an anti-cancer therapeutic is administered, CEND-1 is likewise co-administered to facilitate the therapeutics penetration into the tumor. The co-administration per dose of CEND-1 does not need to be exactly simultaneous with the therapeutic agent(s), and CEND-1 can be administered either before or after the administration of the therapeutic agent.

In certain embodiments, CEND-1 is administered before or during the administration of anti-cancer therapy, wherein the cancer therapy is at a dosing regimen selected from the group consisting of: 4 times/day, 3 times/day, twice daily, once daily, once every other day, once every 2nd day, once every 3rd day, once every 4th day, once every 5th day, once every 6th day, once weekly, once every 8th day, once every 9th day, once every 10th day, once every 11th day, once every 12th day, once every 13th day, once every 2 weeks, once every 3 weeks, and/or once per month. In one embodiment, CEND-1 is present in a dry formulation or suspended in a biocompatible medium.

In particular embodiments, the biocompatible media is selected from the group consisting of: water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, and lipid-containing emulsions. In a particular embodiment, CEND-1 is administered intravenously.

The method of the present invention is particularly suitable for the treatment of pancreatic cancer, which is characterized by a prominent dense tumor stroma, acting as a physical barrier to drug entry. Therefore, advanced pancreatic cancer was chosen as the first clinical indication for CEND-1. As an example of clinical usefulness, we show safety and efficacy results of CEND-1 when given alone or in combination with nab-paclitaxel and gemcitabine, including its ability to enhance tumor response.

Also provided herein is a method of treating pancreatic cancer in a patient in need thereof, comprising administering to the patient an effective amount of CEND-1, in combination with gemcitabine and/or nab-paclitaxel, or pharmaceutically acceptable salts thereof. In certain embodiments, the pancreatic cancer is selected from the group consisting of: primary pancreatic cancer, metastatic pancreatic cancer, refractory pancreatic cancer, cancer drug resistant pancreatic cancer and adenocarcinoma. In a particular embodiment, the cancer is ductal adenocarcinoma (Stage 0-IV).

In another embodiment the afore described CEND-1 for use in the treatment of pancreatic cancer can be administered in combination with at least one additional anti-cancer drug, which preferably is known to be effective against pancreatic cancer, such as gemcitabine. In context of the present invention it was found that using a CEND-1 can enhance the clinical activity of other pancreatic cancer drugs such as gemcitabine and nab-paclitaxel administered by the intravenous route.

Also provided herein is a method of treating pancreatic cancer, colon cancer or appendiceal cancer in a patient in need thereof, comprising administering to the patient an effective amount of CEND-1, in combination with Folfirinox and/or Panitumumab, or pharmaceutically acceptable salts thereof. In certain embodiments, the pancreatic cancer is selected from the group consisting of: primary pancreatic cancer, metastatic pancreatic cancer, refractory pancreatic cancer, cancer drug resistant pancreatic cancer and adenocarcinoma. In a particular embodiment, the cancer is ductal adenocarcinoma (Stage 0-IV).

As used herein, the term "FOLFIRINOX," FOLFIRINOX regimen, or grammatical variations thereof refers to the well-known combination of each of Oxaliplatin, Leucovorin calcium (folinic acid), Irinotecan hydrochloride and Fluorouracil, in the context of cancer treatments. In other embodiments, FOLFIRINOX-based combinations can be used, such, Folfox, which corresponds to oxaliplatin, Leucovorin calcium (folinic acid), and Fluorouracil; and Folfiri, which corresponds to Leucovorin Calcium (folinic acid), Fluorouracil, and Irinotecan hydrochloride.

In another embodiment the afore described CEND-1 for use in the treatment of pancreatic cancer can be administered in combination with at least one additional anti-cancer drug, which preferably is known to be effective against pancreatic cancer, such as gemcitabine. In context of the present invention it was found that using a CEND-1 can enhance the clinical activity of other pancreatic cancer drugs such as gemcitabine and nab-paclitaxel administered by the intravenous route In certain embodiments, CEND-1 is administered in an amount selected from the group consisting of: about 0.2 to 20 mg/kg body weight/per dose of cancer therapy, about 0.3 to 17 mg/kg body weight/per dose of cancer therapy, about 0.4 to 14 mg/kg body weight/per dose of cancer therapy, about 0.5 to 11 mg/kg body weight/per dose of cancer therapy, about 0.6 to 8 mg/kg body weight/per dose of cancer therapy, about 0.7 to 5 mg/kg body weight/per dose of cancer therapy, about 0.8 to 3.2 mg/kg body weight/per dose of cancer therapy. In once embodiment, CEND-1 is administered in an amount corresponding to 3.2 mg/kg body weight/per dose of cancer therapy.

In particular embodiments, CEND-1 is administered before or during the administration of anti-cancer therapy, wherein the cancer therapy is at a dosing regimen selected from the group consisting of: 4 times/day, 3 times/day, twice daily, once daily, once every other day, once every 2nd day, once every 3rd day, once every 4th day, once every 5th day, once every 6th day, once weekly, once every 8th day, once every 9th day, once every 10th day, once every 11th day, once every 12th day, once every 13th day, once every 2 weeks, once every 3 weeks, and/or once per month. In a particular embodiment for treating pancreatic cancer.

CEND-1 is administered in a range amount selected from: 0.01-100, 0.02-90, 0.03-80, 0.04-70, 0.05-60, 0.06-50, 0.07-40, 0.08-30, 0.09-30, 0.1-25, 0.11-20, 0.12-15, 0.13-10, 0.14-9, 0.15-8, 0.16-7, 0.17-6, 0.18-5, 0.19-4, or 0.2-3.2 mg/kg body weight/day or per dose of chemotherapy;

nab-paclitaxel is administered in a range amount selected from: 1-500, 10-450, 20-400, 30-350, 40-300, 50-250, 60-200, 70-175, 80-160, 90-150, 100-140, 110-140, 115-135 or 120-130 mg/m2; and gemcitabine is administered in a range amount selected from: 1-5000, 100-4500, 200-4000, 300-3500, 400-3000, 500-2500, 550-2000, 600-1750, 650-1500, 700-1400, 750-1300, 800-1200, or 900-1100 mg/m2.

In yet another embodiment for treating pancreatic cancer: CEND-1 is administered in a range of 0.2-3.2 mg/kg body weight/day or per dose of chemotherapy; nab-paclitaxel is administered at 125 mg/m2; and gemcitabine is administered at 1000 mg/m2.

In another embodiment for treating either pancreatic, colon and appendiceal cancers, CEND-1 administered in a range amount selected from: 0.01-100, 0.02-90, 0.03-80, 0.04-70, 0.05-60, 0.06-50, 0.07-40, 0.08-30, 0.09-30, 0.1-25, 0.11-20, 0.12-15, 0.13-10, 0.14-9, 0.15-8, 0.16-7, 0.17-6, 0.18-5, 0.19-4, or 0.2-3.2 mg/kg body weight/day or per dose of chemotherapy;

FOLFIRINOX in the form of each of Oxaliplatin, Leucovorin, and Irinotecan are each administered in a range amount selected from: 1-500, 10-450, 20-400, 30-350, 40-300, 50-250, 60-200, 70-175, 80-160, 90-150, 100-140, 110-140, 115-135 or 120-130 mg/m2; and Fluroouracil is administered in a range amount selected from: 1-5000, 100-4500, 200-4000, 300-3500, 400-3000, 500-2500, 550-2000, 600-1750, 650-1500, 700-1400, 750-1300, 800-1200, or 900-1100 mg/m2;

and/or pantitumab is administered in a range amount selected from: 0.01-100, 0.02-90, 0.03-80, 0.04-70, 0.05-60, 0.06-50, 0.07-40, 0.08-30, 0.09-30, 0.1-25, 0.11-20, 0.12-15, 0.13-10, 0.14-9, 0.15-8, 0.16-7, 0.17-6, 0.18-5, 0.19-4, or 0.2-3.2 mg/kg body weight/day or per dose of chemotherapy; or 1-20 mg/kg per 14 days; 2-15 mg/kg per 14 days; 3-12 mg/kg per 14 days; 4-10 mg/kg per 14 days, 5-8 mg/kg per 14 days; or 6 mg/kg per 14 days.

In yet another embodiment for treating either pancreatic, colon and appendiceal cancers: CEND-1 is administered in a range of 0.2-3.2 mg/kg body weight/day or per dose of chemotherapy; Oxaliplatin is administered at 85 mg/m2. Leucovorin is administered at 400 mg/m2, Irinotecan is administered at 180 mg/m2; and Fluorouracil is administered at 2400 mg/m2; and/or pantitumab is administered at 6 mg/kg per 14 days.

In certain embodiments of the invention methods provided herein, efficacy or clinical activity of the method is measured by determining: Overall Response Rate (ORR), Progression Free Survival (PFS) and/or Overall Survival (OS). In yet further embodiments, efficacy or clinical activity of the method is measured by determining one or more of: an Overall Response Rate (ORR) selected from greater than 25%, 30%, 35%, 40%, 45%, 50%, 55%, 60%, 65%, 70%, 75%, 80%, 85%, 90%, or greater that 95%; a Progression Free Survival (PFS) selected from greater than 25%, 30%, 35%, 40%, 45%, 50%, 55%, 60%, 65%, 70%, 75%, 80%, 85%, 90%, or greater that 95%; and/or an Overall Survival (OS) selected from greater than 25%, 30%, 35%, 40%, 45%, 50%, 55%, 60%, 65%, 70%, 75%, 80%, 85%, 90%, or greater that 95%.

Also provided herein are pharmaceutical composition comprising: an iRGD-analog and a pharmaceutically acceptable excipient. In an embodiment, the iRGD-analog is CEND-1. Pharmaceutically acceptable excipients are well-known in the art. The CEND-1 compositions can be administered to an individual (such as human) via a bolus injection or an infusion, via various routes, including, for example, intravenous, intra-arterial, intraperitoneal, intrapulmonary, oral and inhalation, subcutaneous. In some embodiments, the composition is administered intravenously.

The formulations can be presented in unit-dose or multi-dose sealed containers, such as ampules and vials, and can be stored in a freeze-dried (lyophilized) condition requiring only the addition of the sterile liquid excipient, for example, saline, for injections, immediately prior to us.

In particular embodiments, CEND-1 for injection is a sterile, white, lyophilized powder supplied as 100 mg per vial of active ingredient dose strength for intravenous administration. CEND-1 Injection consists of CEND-1 drug substance with sodium acetate trihydrate and mannitol as excipients.

In a particular embodiment, the invention composition corresponds to the iRGD-analog set forth as the structure in FIG. 2 (CEND-1). The invention iRGD-analog differs from the prior art iRGD peptides in the specific moieties used to block the amino and carboxy termini, which has resulted in significant advantages over prior art cyclic iRGD peptides. In some embodiments, the moieties are acetyl groups and carboxyamide groups. In some embodiments, the N-terminal amine is acetylated and the C-terminal carboxyl is amidated. In some embodiments, the N-terminal amino group is blocked by an acetyl group and the C-terminal carboxy terminus, i.e., the C-terminal carbonyl group, is blocked by a carboxyamide group. For example, the invention iRGD-analog (set forth in FIG. 2 as CEND-1) has the following molecular formula $C_{37}H_{60}N_{14}O_{14}S_2$; a MW 989.1; and the recent CAS Registry #: 2580154-02-3. Whereas one prior art iRGD with at least one inferior therapeutic property corresponds to an "academic" or "conventional" iRGD having the molecular formula: $C_{35}H_7N_{13}O_{14}S_2$; a molecular weight of 948.04; and CAS Registry No. 1392278-76-0. In some embodiments, D-amino acids are used in the peptide rather than L-amino acids. In some embodiments, modified amino acids known in the art are used rather than unmodified amino acids; such modifications can include those described by Wang (Current Biotechnology, Volume 1, Number 1, 2012, pp. 72-79(8)), incorporated in its entirety herein by reference.

Advantages of the invention CEND-1 iRGD-analog (FIG. 2; $C_{37}H_{60}N_{14}O_{14}S_2$; MW 989.1), relative to prior art CAS Registry No. 1392278-76-0 cyclic peptide and other known iRGD molecules, while maintaining favorable in vitro/in vivo potency and/or efficacy, include one or more of the following:

Favorable pharmacokinetic properties;
Improved stability in plasma/serum;
Improved stability in formulated solution;
Improved stability in storage; and/or
Improved protection from proteases such as aminopeptidases and carboxypeptidases.

In certain embodiments, favorable and/or improved pharmacokinetic properties are selected from one or more of absorption, distribution, metabolism, and/or excretion. In particular embodiments, CEND-1 has a degradation rate 3-fold lower (i.e., improved stability) than the degradation rate of iRGD in phosphate buffered saline, 37° C. and pH=7.4. In a further embodiment, CEND-1 has a degradation rate 1.6-fold lower (i.e., improved stability) than the degradation rate of iRGD in in pooled human plasma.

As used herein, the phrase "while maintaining favorable in vitro/in vivo potency and/or efficacy" refers to the continued effect of CEND-1 on the respective therapeutic agents, such that the efficacy and/or potency is not diminished by CEND-1.

Also provided herein is a kit or composition comprising an iRGD-analog (CEND-1); and an anti-cancer agent. The kit, wherein the iRGD-analog is set forth as the structure in FIG. 2.

Also provided herein are methods of manufacturing iRGD-analogs including CEND-1. In embodiments, iRGD-analogs including CEND-1 are chemically synthesized using currently available laboratory equipment using either Fmoc (9-fluorenylmethyloxycarbonyl) or Boc (tert-butyloxycarbonoyl) chemistry. Alternatively, the iRGD-analogs including CEND-1 are synthesized through cell-free expression systems or using mammalian, microbial, insect, or avian cells according to biomanufacturing methods known to those in the art. Boc/Bzl protection, when utilized with in situ neutralization, can provide superior results for long or difficult peptide sequences. Cleaving the peptide product from the resin requires strong acids such as TFMSA or HF. Fmoc/tBu protection typically does not require reagents stronger than 50% TFA to remove side-chain protecting groups and cleave the peptide from the resin support, hence it can be scaled up easily in the laboratory. The side chains can be deprotected while the N-terminal Fmoc remains in place, allowing side chain modification. In addition, there are a variety of other side chain protecting groups available which allow selective deprotection at a specific site.

The acetylation and amidation modifications described herein are also applied according to methods known to those skilled in the art. In embodiments, the C-terminal amides are prepared on an amide-forming resin such as MBHA, Rink or Sieber resins. In other embodiments, C-terminal amides are formed by cleaving the peptide from the resin by ammonolysis. Although ammonolysis can be performed on many standard resins such as Merrifield and Wang resins, Oxime and HMBA resins are preferred. In embodiments, N-terminal acetylation is achieved by adding a final capping step to the peptide synthesis protocol. In embodiments, the capping is performed using 6 vol % Ac2O and 3 vol % DIPEA in DMF, 2×10 min.

EXAMPLES

Example 1: Stability of CEND-1 Compared to Non-Acetylated, Non-Amidated iRGD The effects of the acetylation of the N-terminal end of CEND-1 (FIG. 2) and the amidation of the C-terminal end of CEND-1 on its stability in phosphate-buffered saline, pooled human plasma, and in the presence of carboxypeptidase and aminopeptidase were evaluated. CEND-1 (CAS Registry No: 2580154-02-3) was compared to "conventional" cyclic iRGD (CAS No. 1392278-76-0), which is non-acetylated and non-amidated.

Methods:

For the stability studies in phosphate-buffered saline (PBS), pH=7.4, the 10×PBS stock was diluted to normal 1×PBS concentration and CEND-1 or iRGD was dissolved to a final concentration of ~1 mg/mL. For the stability studies in pooled human plasma, the frozen pooled human plasma was first thawed, mixed and then clarified by centrifugation. CEND-1 or iRGD was dissolved at a final concentration of ~2.5 mg/mL in clarified pooled human plasma. For the stability studies with carboxypeptidase Y (CY) a 50 mM sodium phosphate buffer at pH=6.5 containing 0.15 M sodium chloride, 6 Units/mL of carboxypeptidase and ~0.1 mg/mL CEND-1 or iRGD was prepared. For the stability studies with carboxypeptidase B (CB) a 25 mM Tris·HCl buffer at pH=7.7 containing 0.10 M sodium chloride, 14 Units/mL of carboxypeptidase B and 0.1 mg/mL CEND-1 or iRGD was prepared. For the stability studies with aminopeptidase (AP) a 20 mM Tris·HCl buffer at pH=8 containing 10 Units/mL of carboxypeptidase B and ~0.1 mg/mL CEND-1 or iRGD was prepared.

The solutions were incubated at 25° C. and 37° C. and samples were pulled at appropriate time intervals for analysis. Samples in PBS, samples with carboxypeptidase Y and B and aminopeptidase were directly used for HPLC analysis without prior dilution. The samples containing pooled human plasma (0.1 mL) were diluted with 0.15 mL 0.1% trifluoracetic acid in methanol, mixed and centrifuged to remove insoluble plasma proteins.

Figure 3:
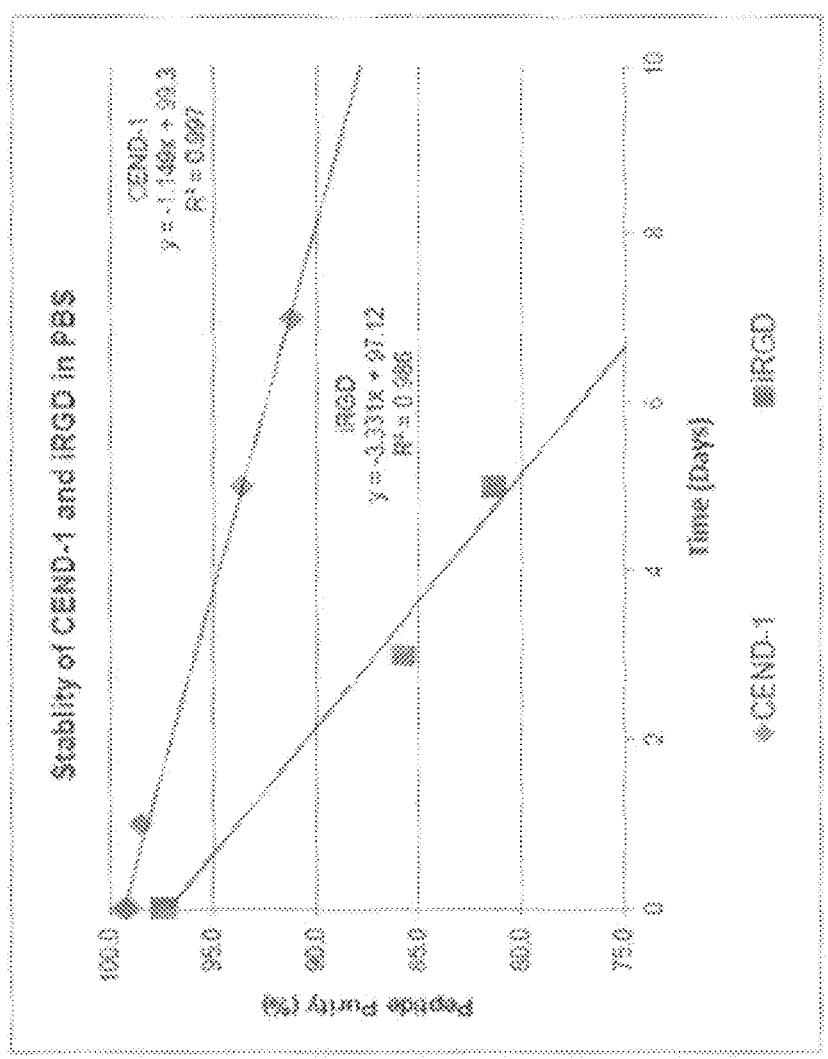
FIG. 3 shows the stability of CEND-1 and iRGD in phosphate-buffered saline, pH=7.4.

Results:

At 37° C. CEND-1 degraded at a rate of 1.1% per day in phosphate buffered saline, pH=7.4 (FIG. 3). At 37° C. iRGD degraded at a rate 3.3% per day in phosphate buffered saline, pH=7.4 (FIG. 3). The ratio of the degradation rate between iRGD and CEND-1 is 3-fold demonstrating that CEND-1 is more stable in phosphate buffered saline, pH=7.4 as compared to iRGD (Table 1).

TABLE 1

Stability of CEND-1 and iRGD in PBS and plasma.

| Compound | Condition | Degradation Rate (%/Day) | Ratio Deg Rate iRGD/CEND-1 |
|---|---|---|---|
| CEND-1 | Phosphate-buffered saline, pH = 7.4 | 1.1 | 3 |
| iRGD | Phosphate-buffered saline, pH = 7.4 | 3.3 | 3 |
| CEND-1 | Pooled human plasma | 2.5 | 1.6 |
| iRGD | Pooled human plasma | 4.0 | 1.6 |

Figure 4:
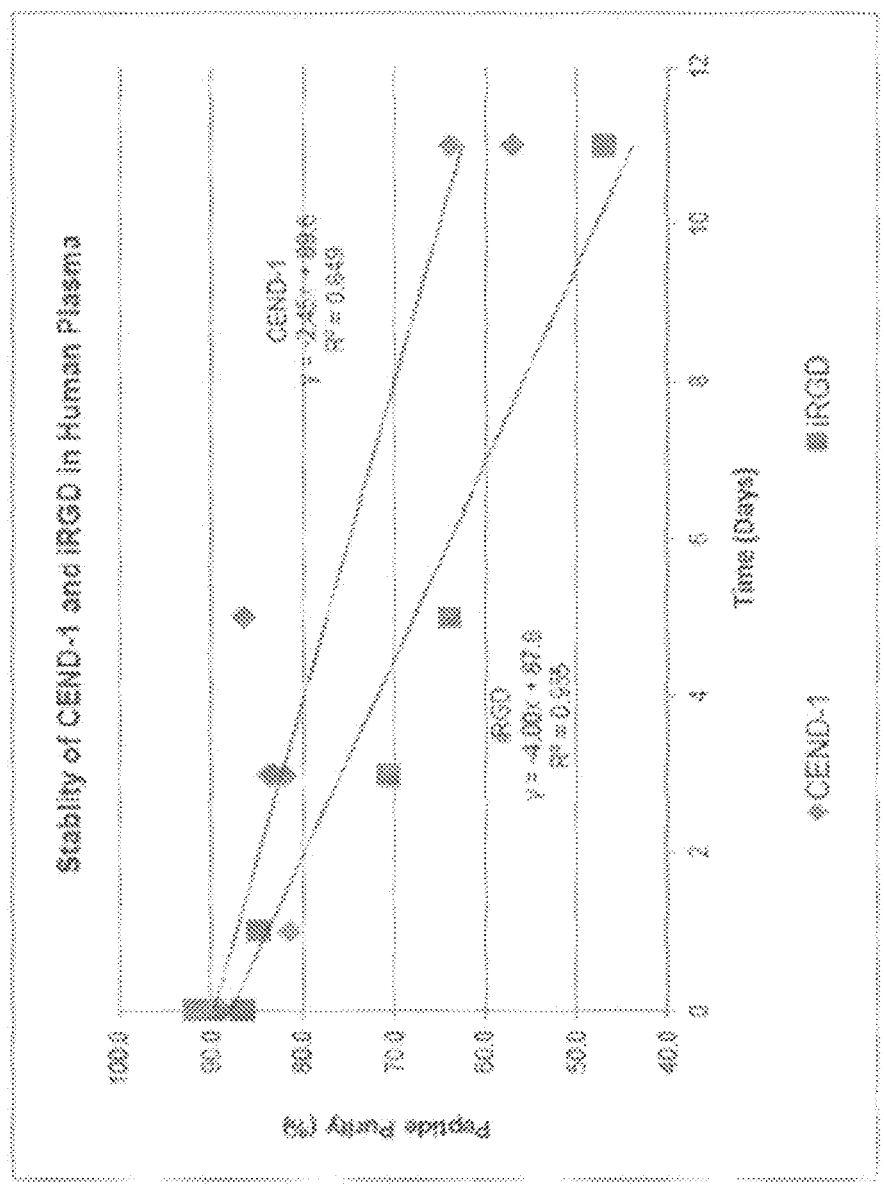
FIG. 4 shows the stability of CEND-1 and iRGD in in pooled human plasma by concentration.

At 37° C. CEND-1 degraded at a rate of 2.5% per day in pooled human plasma (FIG. 2). At 37° C. iRGD degraded at a rate of 4% per day in pooled human plasma (FIG. 4). The ratio of the degradation rate between iRGD and CEND-1 in human plasma is 1.6 demonstrating that CEND-1 is more stable in pooled human plasma than iRGD (Table 1).

Figure 5:
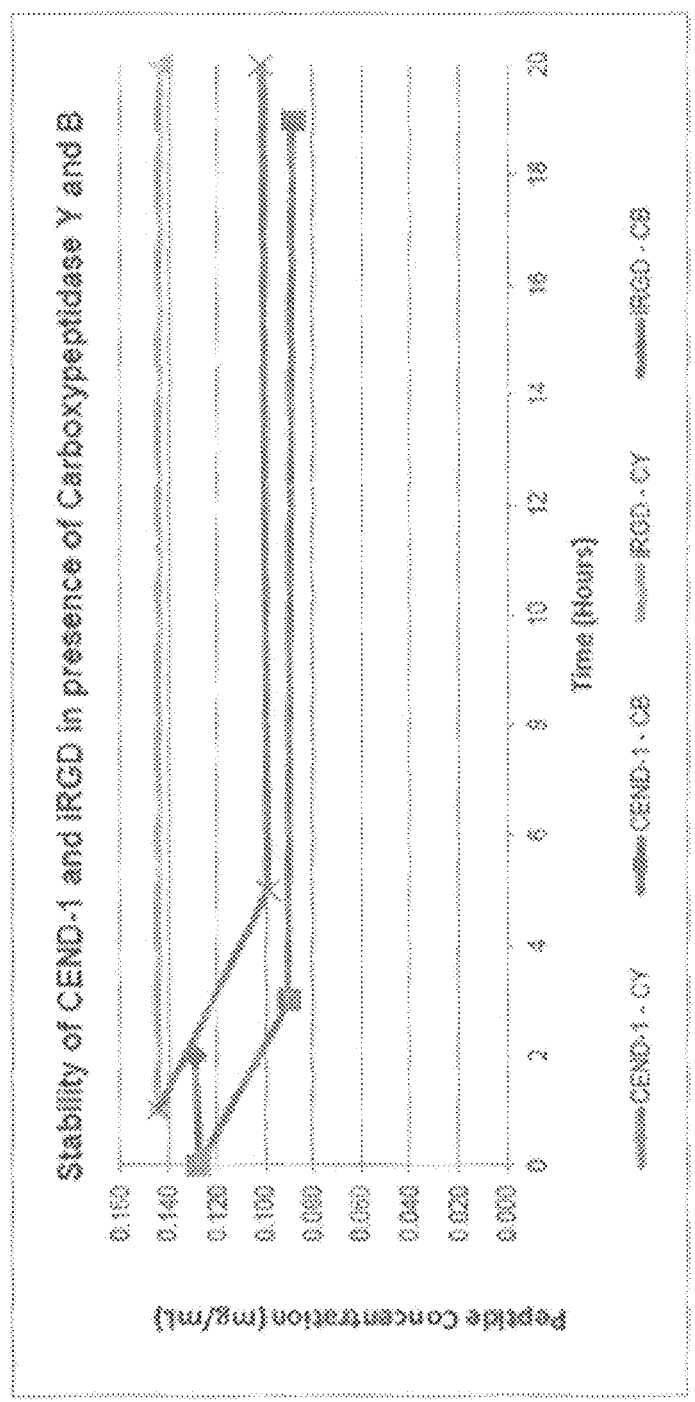
FIG. 5 shows the stability of CEND-1 and iRGD in presence of carboxypeptides Y and B.
Figure 6:
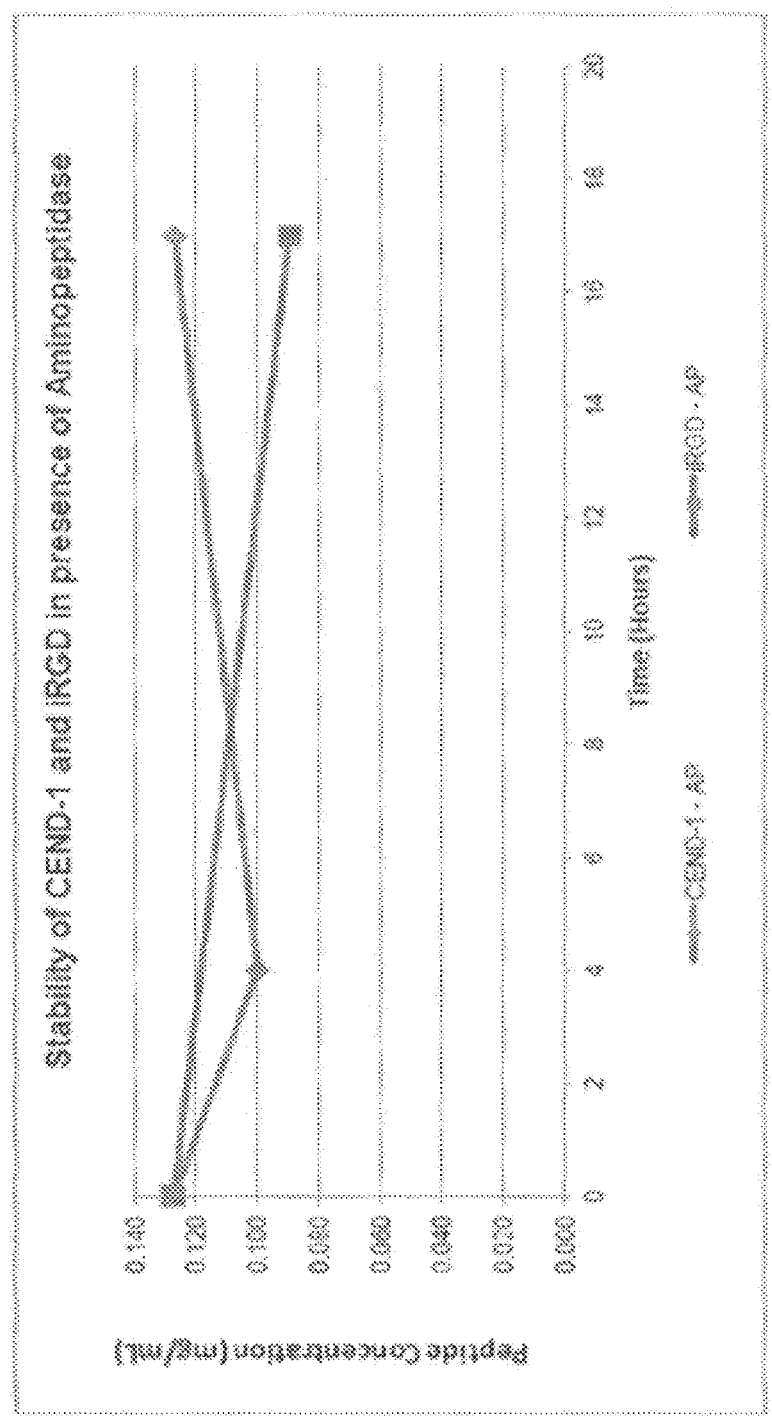
FIG. 6 shows the stability of CEND-1 and iRGD in the presence of aminopeptidase.

Carboxypeptides Y and B neither degraded CEND-1 nor iRGD at 25° C. in the respective buffers as recommended by the enzymes' suppliers (FIG. 5). The purity of CEND-1 and iRGD was not affected by the enzymes. Aminopeptidase neither degraded CEND-1 nor iRGD at 25° C. in a buffer recommended by the enzyme's supplier (FIG. 6). The purity of CEND-1 and iRGD were not affected by the enzymes.

Conclusions

In phosphate buffered saline (PBS) (pH=7.4) CEND-1 was more stable as compared to iRGD by three-fold (300%) when incubated at 37° C. In pooled human plasma CEND-1 was more stable as compared to iRGD by 1.6-fold (60%) when incubated at 37° C. Carboxypeptidase Y and B did not degrade appreciatively CEND-1 or iRGD at 25° C. in buffers recommended by the enzymes' manufacturers. Aminopeptidase did not degrade appreciatively CEND-1 or iRGD at 25° C. in a buffer recommended by the enzyme's manufacturer.

Thus, iRGD is less stable in PBS and pooled human plasma as compared to CEND-1. The stability of both CEND-1 and iRGD is not affected by the carboxypeptidases used and the aminopeptidases. Cyclization of peptides may make them resistant to carboxypeptidases and aminopeptidases. Linear forms of CEND-1 and iRGD may be less resistant to carboxypeptidase and aminopeptidases.

Example 2: Pharmacokinetic Study in Mice

This example demonstrates the favorable pharmacokinetic properties of CEND-1 over iRGD, including increased half-life, in vivo. CEND-1 or iRGD was given to fed CD-1 ICR mice by IV bolus at a nominal dose of 4.5 mg/kg in both groups, with four mice in each group, and an actually administered dose of 3.87 mg/kg for CEND-1 and 4.33 mg for iRGD. CEND-1 and iRGD were formulated in saline at a concentration of 0.9 mg/ml. Liquid chromatography-mass spectroscopy (LC-MS) was used to determine plasma levels of CEND-1 and iRGD in mice at different time points. Pharmacokinetic parameters were then calculated. At 1 hour after administration, the mean plasma concentration of iRGD was 209 ng/ml, whereas that of CEND-1 was 535 ng/ml, representing a 2.56-fold increase. The half-life was calculated as 0.243 h for CEND-1 and 0.167 h for iRGD, which corresponds to CEND-1 having a 46% increased half-life compared to prior art iRGD in vivo. This unexpected increase in half-life is expected to provide a significantly enhanced therapeutic effect for CEND-1.

TABLE 2

Plasma concentration of CEND-1 and iRGD after administration of a bolus dose of 4.5 mg/kg.

| Time (h) | Mean Cmax plasma CEND-1 concentration (ng/ml) | Standard deviation | Coefficient of variance | Mean Cmax plasma iRGD concentration (ng/ml) | SD | Coefficient of variance |
|---|---|---|---|---|---|---|
| 0.05 | 9561 | 1917 | 20.1 | 11497 | 1034 | 8.99 |
| 0.167 | 5756 | 1777 | 30.9 | 6943 | 1421 | 20.5 |
| 0.5 | 1917 | 425 | 22.2 | 1786 | 196 | 11.0 |
| 1.0 | 535 | 182 | 33.9 | 209 | 47.0 | 22.5 |
| 1.5 | 121 | 77.0 | 63.6 | Not measured | Not determined | Not determined |
| 4.0 | Below quantifiable limit | Not determined | Not determined | Not measured | Not determined | Not determined |

TABLE 3

Pharmacokinetic parameters for CEND-1 and iRGD after administration of a bolus dose of 4.5 mg/kg.

| Pharmacokinetic parameters | Mean for CEND-1 | Standard deviation | Coefficient of variation | Mean Cmax for IRGD | Standard deviation | Coefficient of variation |
|---|---|---|---|---|---|---|
| $C_0$ (ng/mL) | 11908 | 1851 | 15.5 | 14408 | 1953 | 13.6 |
| $T_{1/2}$ (h) | 0.243 | 0.0493 | 20.3 | 0.167 | 0.0137 | 8.23 |
| $T_{last}$ (h) | 1.50 | — | — | 1.00 | — | — |

Example 3: Phase I Trial (Referred to as CEND-001 Trial) of CEND-1 in Combination with Gemcitabine and Nab-Paclitaxel in Patients with Metastatic Pancreatic Cancer This example demonstrates that CEND-1 was well tolerated in combination with gemcitabine and nab-paclitaxel and provided clinical benefit in patients with advanced pancreatic cancer. When compared to benchmark trials, the response rates are more than doubled. CEND-1 is also referred to herein as the iRGD-analog corresponding to the chemical structure set forth in FIG. 2 and CAS Registry #2580154-02-3.

Materials:

CEND-1 drug product is a synthetic peptide manufactured using solid phase peptide synthetic techniques with high chemical purity. CEND-1 for Injection is a sterile, white, lyophilized powder supplied as 100 mg per vial of active ingredient dose strength for intravenous administration. CEND-1 Injection consists of CEND-1 drug substance with sodium acetate trihydrate and mannitol as excipients.

Methods:

The open-label, dose escalation, multicenter (3 active sites in Australia) trial involved a run-in phase with ascending doses of CEND-1 monotherapy (1-7 days), followed by the combination of CEND-1 with nab-paclitaxel (125 mg/m$^2$) and gemcitabine (1000 mg/m$^2$) on days 1, 8, 15 of a 21-day treatment cycle. Patients will first receive the intravenous infusion of nabpaclitaxel (125 mg/m$^2$ over 30 minutes (±3 minutes)). CEND-1 is given intravenously at the applicable dose level as a slow IV push over 1 minute (±30 seconds) immediately following completion of the post-nabpaclitaxel saline flush. The intravenous infusion of gemcitabine (1000 mg/m2 over 30 minutes (±3 minutes)) will be started as soon as possible, but at the latest within 10 minutes of CEND-1 administration.

| Safety/Dose Escalation (Cohort 1a) | | |
|---|---|---|
| Dose Level | Run-in (7 days) | Treatment (28-day cycle) |
| 1 (1-6 pts) | CEND-1 0.2 mg/kg | nabpaclitaxel 125 mg/m$^2$ CEND-1 0.2 mg/kg gemcitabine 1000 mg/m$^2$ |
| 2 (1-6 pts) | CEND-1 0.8 mg/kg | nabpaclitaxel 125 mg/m$^2$ CEND-1 0.8 mg/kg gemcitabine 1000 mg/m$^2$ |
| 3 (3-6 pts) | CEND-1 1.6 mg/kg | nabpaclitaxel 125 mg/m$^2$ CEND-1 1.6 mg/kg gemcitabine 1000 mg/m$^2$ |
| 4 (3-6 pts) | CEND-1 3.2 mg/kg | nabpaclitaxel 125 mg/m$^2$ CEND-1 3.2 mg/kg gemcitabine 1000 mg/m$^2$ |

Patients (n=31) who had measurable metastatic pancreatic cancer, no prior treatments for metastatic disease and an ECOG PS of 0 to 1 were included. Primary endpoints are safety and optimal biologic dose, secondary and exploratory endpoints included response rates, pharmacokinetics and biomarkers.

Results: 29 patients completed the first treatment cycle and were evaluable for response (data cutoff, 27 Apr. 2020). No dose limiting toxicities were observed. AEs were generally consistent with those of nabpaclitaxel and gemcitabine. The only drug related grade (gr) 3-4 adverse events (AEs) present in >3 patients were neutropenia in 18 (62%) and anemia in 5 (17%) patients. By investigator assessed RECIST 1.1 criteria, 1 pt had a complete response (3.4%), 16 pt. with partial response (55%), 10 pt. with stable disease (34%), and 2 pt. with progressive disease (6.9%). Among the patients with elevated CA19-9 with a postbaseline assessment available, A total of 96% of the patients had a decrease from baseline of at least 20%, and 74% had a decrease of at least 90% and/or had the CA19-9 levels normalized to baseline.

Conclusions: Administration of CEND-1 in combination with nab-paclitaxel and gemcitabine is safe, with no dose-limiting toxicities. The incidence of Grade 3 and 4 Adverse Event is lower than in similar published trials. The median duration of treatment was longer and the response rates were >2 times higher than in the benchmark trials.

| BASELINE SUBJECT CHARACTERISTICS | |
|---|---|
| Age | |
| Median | 62 |
| Min-Max | 42-80 |
| Distribution—no. (%) | |
| <65 yr | 15 |
| ≥65 yr | 14 |
| Sex—no. (%) | |
| Female | 11 |
| Male | 18 |
| Race or ethnic group—no.(%) | |
| Asian | 2 |
| White | 25 |
| Other | 2 |
| ECOG Performance Score | |
| 0 | 10 |
| 1 | 19 |

Frequencies below are compared with iMPACT3 trial, data in parenthesis (Von Hoff et al., 2013).

Efficacy Results—Response Rates

The overall response rate (ORR) for all evaluable patients (N=29) was 59% (vs. 23%). The overall disease control rate for 16 weeks was 79% (vs. 48%).

Figure 1:
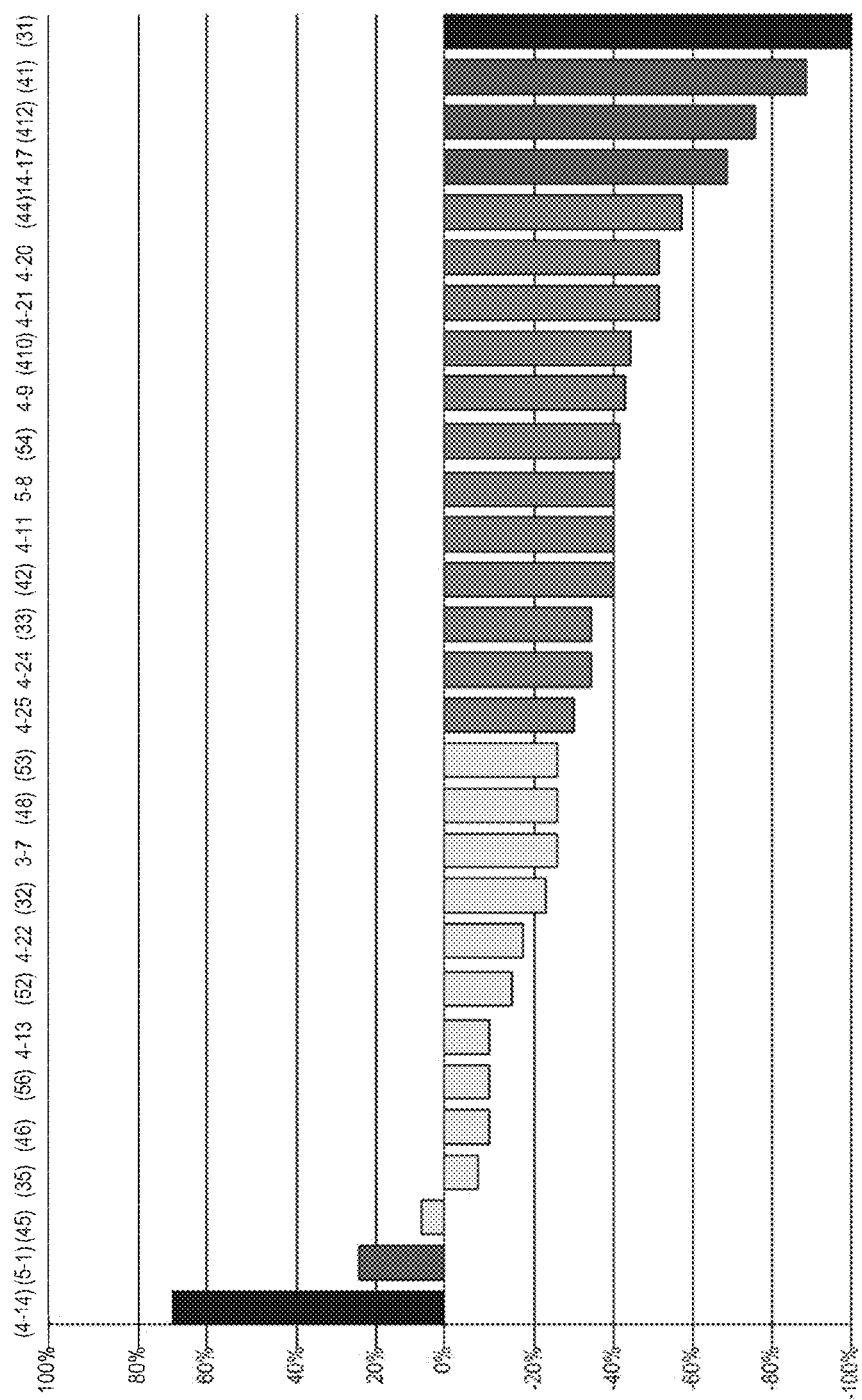
FIG. 1 shows a waterfall plot described in Example 2.

FIG. 1 corresponds to a waterfall plot of maximum percentage changes from baseline in the size of target lesions according to the Response Evaluation Criteria In Solid Tumors 1.1. A total of 16 patients exhibited partial response (55%) and 10 patients had stable disease (34%).

CA19-9

A total of 24 patients had an elevated baseline CA19-9 (>37 U/L). Of these, 23 patients had at least one on-treatment CA19-9 measurement. A total of 96% of the patients had a decrease from baseline of at least 20% (vs. 61%), and 74% had a decrease of at least 90% and/or had the CA19-9 levels normalized to baseline.

At study closure, median (IQR) PFS was 9.7 months [6.2-11.6], and median OS was 13.2 [9.7-22.5] months.

Treatment Exposure

Safety

Table 2 below shows frequencies of bone marrow toxicity observed according to the National Cancer Institute Common Terminology Criteria for Adverse Events (CTCAE), version 5. The frequency of grade 3-4 bone marrow toxicity in this material was 55% for neutropenia, 14% for leukopenia, 3% for thrombocytopenia and 24% for anaemia.

CEND1-001 Study

In the CEND1-001 trial, as set forth above, CEND-1 was given initially at escalating doses from 0.2 mg/kg to 3.2 mg/kg during a run-in period of 1 to 7 days, during which PK and safety of the single agent were assessed.

There were 8 patients in Cohort 1a: 1 patient at dose level 1 (CEND-1 0.2 mg/kg), 1 patient at dose level 2 (0.8 mg/kg), 3 patients at dose level 3 (1.6 mg/kg) and 3 patients at dose level 4 (3.2 mg/kg). There were 23 patients in Cohort 1b, 11 patients at dose level 3 (1.6 mg/kg), 11 patients at dose level 4 (3.2 mg/kg), and 1 patient who was assigned to dose level 4 (3.2 mg/kg) but withdrew from the study following the run-in period and only received the run-in dosing with CEND-1 0.2 mg/kg.

Of the 31 patients enrolled, 29 were evaluated for efficacy, 31 were evaluated for PK and 30 were evaluated for PD (N=14 at the 1.6 mg/kg CEND-1 dose and N=14 at the 3.2 mg/kg CEND-1 dose level, not including the 2 patients in the CEND-1 low dose group). There were 10 patient deaths reported during the study, 9 caused by progression of primary disease (metastatic pancreatic cancer) and 1 due to a left middle cerebral artery stroke (approximately 3 months after the last CEND-1 dose).

Confirmed objective responses (OR) occurred in 17/29 (58.6%) patients (95% CI=38.9, 76.5). Overall, the number of patients with progression was 16/29 (55.2%) and the median time to progression was approximately 9.7 months.

These response rates (OR) are clearly above and a marked improvement over what has been achieved in comparable trials historically, Table 3. In the Phase 3 registration trial for nab-paclitaxel, the response rate in first-line metastatic pancreatic cancer patients treated with the gemcitabine/nab-paclitaxel combo was 23% and the PFS 5.5 months (Von Hoff et al., 2013).

TABLE 5

Outcomes of Gemcitabine and Nab-Paclitaxel in Metastatic Pancreatic Cancer
Gemcitabine and Nab-Paclitaxel Arm

| Study | Stage | Investigational Agent | Phase | N (Placebo) | ORR (%) | mOS (months) | mPFS (months) | PFS 6 m (%) | PFS 1 Y (%) |
|---|---|---|---|---|---|---|---|---|---|
| VonHoff 2013-International | IV | Gem vs Gem/NP | 3 | 432 | 23 | 8.5 | 5.5 | 45* | 17* |
| Renouf 2020-Canada | IV | Durvalumab and Tremelimumab | 2 | 61 | 23 | 8.8 | 5.4 | 40* | 18* |
| Van Custem 2020-International | IV | PEGPH20 | 2 | 165 | 36 | 11.5 | 7.1 | 52* | 23* |
| Hu 2019-USA | IV | Tarextumab | 2 | 88 | 31.8 | 7.9 | 5.5 | 38* | 11* |
| Karasic 2019-USA | III/IV | Hydroxychloro-quine | 2 | 57 | 21.1 | 12.1 | 6.4 | 15* | 50** |

TABLE 5-continued

Outcomes of Gemcitabine and Nab-Paclitaxel in Metastatic Pancreatic Cancer
Gemcitabine and Nab-Paclitaxel Arm

| Study | Stage | Investigational Agent | Phase | N (Placebo) | ORR (%) | mOS (months) | mPFS (months) | PFS 6 m (%) | PFS 1 Y (%) |
|---|---|---|---|---|---|---|---|---|---|
| Tempero 2019-International | IV | Ibrutinib | 3 | 213 | 42 | 10.8 | 6.0 | 50* | 19* |

Because of the trend for an improved outcome with the 3.2 mg/kg dose level, this was chosen as the dose for further exploration in future studies.

Tumor Biomarkers

The number of patients with a ≥50% reduction in CA19-9 from Baseline increased to a high of 20/22 (90.9%) patients at Cycle 5 Day 1.

Tumor biomarker results of CEND-1 at the dose levels of 1.6 mg/kg and 3.2 mg/kg show a trend of decreasing CA values over successive cycles of dosing. This supports the further development of CEND-1, in combination with drugs such as Nab-paclitaxel and Gemcitabine, in patients with metastatic cancers.

CEND-1 Pharmacokinetics

Overall, the median Tmax for CEND-1 was 0.067 hours over all days of PK sampling (minimum was 0.03, maximum 0.55). There was dose proportional increase in Cmax without increase with repeat dosing.

Assessment of plasma CEND-1 parameters demonstrated that exposure (AUC0-t, AUC0-6 h and AUC0-inf) followed the same pattern described for Cmax with a trend to increase with increased dose. Dose normalized PK parameters (AUC0-t/D, AUC0-6h/D and AUC0-inf/D) were similar between visits and doses.

CEND-1 was eliminated with median T1/2 values between 1.6 hours and 1.8 hours over all days of PK sampling. CL mean values were between 106.8 mL/h/kg and 266.5 mL/h/kg. The terminal volume of distribution (Vz) mean values were between 220.9 mL/kg and 277.4 mL/kg over all days of PK sampling CEND-1 Safety During the CEND-1 run-in during dose escalation, the following definition of DLT was used:

CEND-1 Monotherapy:
  A DLT in the run-in period was defined as:
  Grade 4 neutropenia lasting ≥5 days or Grade 3 or 4 neutropenia with fever and/or infection
  Grade 4 thrombocytopenia (or Grade 3 with bleeding)
  Grade 3 or 4 treatment-related non-hematological toxicity (Grade 3 nausea, vomiting or diarrhea that last >72 hours despite maximal treatment constitutes a DLT, insufficient treatment will not constitute an exception to the DLT criteria, as this would constitute inadequate conduct of the study)
  Dosing delay greater than 2 weeks due to treatment-emergent AEs or related severe laboratory abnormalities.

There were no DLTs or grade 3 or 4 adverse events at any CEND-1 dose level during the single agent run-in portion of the study and no clinically significant adverse events attributable to CEND-1 were reported.

During the combination portion of the study, the following definition of dose-limiting toxicity was used:

Any side effect that is more severe, longer in duration or more frequent than side effects expected from the nab-paclitaxel and gemcitabine package insert.
  Any side effect that is not included in the nab-paclitaxel and gemcitabine package insert that meets the DLT definition of the monotherapy above.

There were no DLTs reported during the study. The majority of TEAEs were CTCAE grade 1 or 2. The number of reported TEAEs at each grade was similar between CEND-1 dose levels. Overall, the severity of TEAEs did not increase with CEND-1 dose. The most common CTCAE grade 3-4 TEAEs by SOC were blood and lymphatic system disorders.

Example 4: A Trial of CEND-1 in Combination with Neoadjuvant FOLFIRINOX Based Therapies in Pancreatic, Colon and Appendiceal Cancers (CENDIFOX)

Cohort 1 Pancreatic Cancer

Biopsy for tissue immune profile if archived tissue not available. Folfirinox infusion for 3 cycles followed by a repeat biopsy for a second tissue immune profiling. Folfirinox plus CEND1 infusion for 3 cycles. Seventy-two hours after last infusion participant will have surgery.

The treatment with CEND-1 will be given as an intravenous (IV) infusion (through a needle in a vein) at the clinic once every 14 days (or Day 1 of every 14-day cycle starting in Cycle 4). FOLFIRINOX is a name for a chemotherapy treatment regimen that includes several different drugs that are given in a certain order, as follows:

All of these drugs are given as an intravenous (IV) infusion (through a needle in a vein) at the clinic once every 14 days (or Day 1 of every 14-day cycle).
  Oxaliplatin—dose is 85 mg/m2 the infusion takes about 2 hours, then
  Leucovorin—dose is 400 mg/m2—this is given at same time with irinotecan (below) and the infusion takes about 1.5 hours.
  Irinotecan—dose is 180 mg/m2—this is given at same time with leucovorin (above), and the infusion takes about 1.5 hours.
  then
  Fluorouracil—dose is 2400 mg/m2—this infusion takes 46 to 48 hours (2 days) with an IV pump done at home.

Cohort 2 Peritoneal Mets

Biopsy for tissue immune profile if archived tissue not available. Folfirinox plus Panitumumab (if RAS/BRAF) infusion for 3 cycles followed by a repeat biopsy for a second tissue immune profiling. Folfirinox plus Panitumumab (if RAS/BRAF positive) and CEND1 infusion for 3 cycles. Seventy-two hours after last infusion participant will have surgery.

The treatment with CEND-1 will be given as an intravenous (IV) infusion (through a needle in a vein) at the clinic once every 14 days (or Day 1 of every 14-day cycle starting in Cycle 4). Patients in need thereof with cancer that has spread to certain areas of the body and who have a certain gene in the tumor called "RAS/BRAF wild type" will receive a therapeutically effective amount of panitumumab in addition to CEND-1 and FOLFIRINOX (as set forth above).

FOLFIRINOX is a name for a chemotherapy treatment regimen that includes several different drugs that are given in a certain order; all of these drugs are given as an intravenous (IV) infusion (through a needle in a vein) at the clinic once every 14 days (or Day 1 of every 14-day cycle), as follows:

Oxaliplatin—dose is 85 mg/m2 the infusion takes about 2 hours, then

Leucovorin—dose is 400 mg/m2—this is given at same time with irinotecan (below) and the infusion takes about 1.5 hours.

Irinotecan—dose is 180 mg/m2—this is given at same time with leucovorin (above), and the infusion takes about 1.5 hours, then Fluorouracil—dose is 2400 mg/m2—this infusion takes 46 to 48 hours (2 days) with an IV pump done at home.

Cohort 3 Oligomets Colon Cancer

Biopsy for tissue immune profile if archived tissue not available. Folfirinox plus Panitumumab (if RAS/BRAF) infusion for 3 cycles followed by a repeat biopsy for a second tissue immune profiling. Folfirinox plus Panitumumab (if RAS/BRAF positive) and CEND1 infusion for 3 cycles. Seventy-two hours after last infusion participant will have surgery.

The treatment with CEND-1 will be given as an intravenous (IV) infusion (through a needle in a vein) at the clinic once every 14 days (or Day 1 of every 14-day cycle starting in Cycle 4). Patients in need thereof with cancer that has spread to certain areas of the body and who have a certain gene in the tumor called "RAS/BRAF wild type" will receive a therapeutically effective amount of panitumumab in addition to CEND-1 and FOLFIRINOX (as set forth above).

FOLFIRINOX is a name for a chemotherapy treatment regimen that includes several different drugs that are given in a certain order; all of these drugs are given as an intravenous (IV) infusion (through a needle in a vein) at the clinic once every 14 days (or Day 1 of every 14-day cycle), as follows:

Oxaliplatin—dose is 85 mg/m2 the infusion takes about 2 hours, then

Leucovorin—dose is 400 mg/m2—this is given at same time with irinotecan (below) and the infusion takes about 1.5 hours.

Irinotecan—dose is 180 mg/m2—this is given at same time with leucovorin (above), and the infusion takes about 1.5 hours. then Fluorouracil—dose is 2400 mg/m2—this infusion takes 46 to 48 hours (2 days) with an IV pump done at home.

The results indicate a favorable outcome with a 90% confidence interval in one or more of the following: Overall survival (OS) will be reported using median survival time; Disease-free survival (DFS) will be reported using median survival time; Overall response rate (ORR); RO resection rate (RORR); and/or Pathological response rate (PCR).

Example 5: Synthetic Process for Preparation of CEND-1 and its Acetate Salt

In general, the synthetic process for the production of CEND-1 or its acetate salt comprises the following stages:
Stage 1: Solid Phase Peptide Synthesis (SPPS)
Stage 2: TFA Cleavage
Stage 3: Cyclization
Stage 4: Salt Exchange Purification
Stage 5: Reconstitution and Final Lyophilization Stage 1: Solid Phase Peptide Synthesis (SPPS)

During SPPS, the sequence of the desired peptide was built up on a polymer support by sequential and repetitive addition of the chosen building blocks. The polymer support comprises cross-linked polystyrene resins (e.g., Rink amide AM resin) which immobilize the growing peptide chains.

Suitably protected amino-acid derivatives were used as building block (Starting Materials). Protection of the reactive α-amino groups relies on the Fmoc strategy. Necessary side-chain protection was achieved by the use of other protecting groups that are stable toward the reagents used for Fmoc-cleavage.

The linear peptide chain was built up from the C-terminus to the N-terminus by repeated cycles until the resin carries the complete amino acid sequence. The repeated cycles comprising:

a) Nα-deprotection with piperidine was used to enable the coupling reaction;

b) Coupling of protected building block (protected amino acid derivatives) in the presence of DIC and Oxymapure as suitable activating reagent(s) for all cycles except cycles in the presence of TCTU and DIPEA for cycle 8, and in the presence of HOBt and DIC for all other cycles in a solvent of DMF, was applied; and c) Mandatory acetylation (capping) of remaining free amino groups using acetic anhydride, and DIPEA in a solvent of DMF, was performed.

Each cycle consists of the following operations:
1) Addition of solvents/reagents to the resin;
2) Stirring of the reaction mixture; and
3) Removal of solvents/reagents by filtration and washing with solvents of DMF and IPA.

After the last coupling step, the peptide resin is washed with IPA and the resin bound peptide is dried under reduced pressure.

The N-terminal acetylation is achieved by adding a final capping step to the peptide synthesis protocol. The capping is performed using 6 vol % $Ac_2O$ and 3 vol % DIPEA in DMF, 2×10 min.

A nine-amino-acid linear peptide with chemical formula: Ac-Cys(Trt)-Arg(Pbf)-Gly-Asp(OMpe)-Lys(Boc)-Gly-Pro-Asp(OMpe)-Cys(Trt)-$NH_2$ on Rink Amide AM Resin was prepared by the synthetic process described in Stage 1.

Stage 2: TFA Cleavage

Cleavage of the peptide from the resin obtained in Stage 1 and simultaneous cleavage of the side-chain protecting groups were accomplished by treatment of the peptide resin with TFA in the presence of suitable scavengers (e.g. $H_2O$, TIS, EDT). After filtering off and washing the resin with TFA, a product was precipitated in cooled IPE. The product was filtered, washed with IPE, and dried under reduced pressure to provide a crude nine-amino-acid linear peptide with chemical formula: Ac-Cys-Arg-Gly-Asp-Lys-Gly-Pro-Asp-Cys-$NH_2$·2TFA, free of resin.

Stage 3: Cyclization to Form a Cyclic Peptide

The crude linear peptide obtained from Stage 2 can be cyclized through intermolecular disulfide bond. Kinetic oxidation of the thiol side chains of Cys residues, using iodine, leads to covalent disulfide bonding of the two Cys thiol side chains.

The crude linear peptide from Stage 2 (the cleavage step) was dissolved in a solution of acetic acid (AcOH). A solution of iodine in methanol (MeOH) was then added dropwise to the crude linear peptide solution to start the oxidation of the Cys residue side chains containing thiols.

The solution was stirred and the reaction was allowed to continue until a red/amber colored solution persists. The reaction was then quenched by dropwise addition of a solution of ascorbic acid in purified water until the red/amber color disappears. A crude cyclic peptide was thus formed.

Stage 4: Salt Exchange Purification by Preparative HPLC (AcOH)

The crude cyclic peptide obtained from Stage 3 was purified by preparative HPLC using a AcOH system on a reversed-phase column with ACN gradient elution and UV detection at 220 nm. The column was first washed with $NH_4OAc$ and AcOH, followed by equilibration with AcOH. Next, the crude cyclic peptide was loaded onto the column and washed with $NH_4OAc$ and AcOH. Finally, the column was washed with AcOH and AcOH in ACN before the product was eluted using a gradient of AcOH in ACN.

The collected fractions were analyzed by HPLC and pooled accordingly. The pooled main fractions were diluted with water to lower their ACN concentration. Side fractions were re-purified. The main fractions were lyophilized.

The combination of the above Stage 3 and Stage 4 provides a purified nine-amino-acid cyclic peptide acetate salt with a chemical formula shown below.

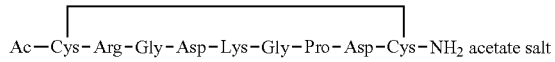

Ac—Cys—Arg—Gly—Asp—Lys—Gly—Pro—Asp—Cys—$NH_2$ acetate salt

Stage 5: Reconstitution and Final Lyophilization

The purified cyclic peptide acetate salt obtained from stage 4 is dissolved in water, microfiltered through a 0.45 m membrane filter, and lyophilized again to yield the final product as a white to off-white powder.

The chemical structure for the neutral form (not in a form of acetate salt) of the cyclic peptide as the final product is shown in FIG. 2, with its stereocenter chirality marked.

The abbreviations of the reagents and solvents mentioned-above are listed below.

ACN=Acetonitrile
EDT=1,2-Ethanedithiol
$NH_4OAc$=Ammonium acetate
$AC_2O$=Acetic anhydride
HOBt=1-Hydroxybenzotriazole
TFA=Trifluoroacetic acid
AcOH=Acetic acid
IPA=Isopropanol
TIS=Triisopropylsilane
DIC=N,N'-Diisopropylcarbodiimide
IPE=Isopropyl ether
DIPEA=Diisopropylethylamine MeOH=Methanol
MeOH=Methanol
DMF=Dimethyl formamide

The invention claimed is:

1. A cyclic peptide with chemical structure as shown below:

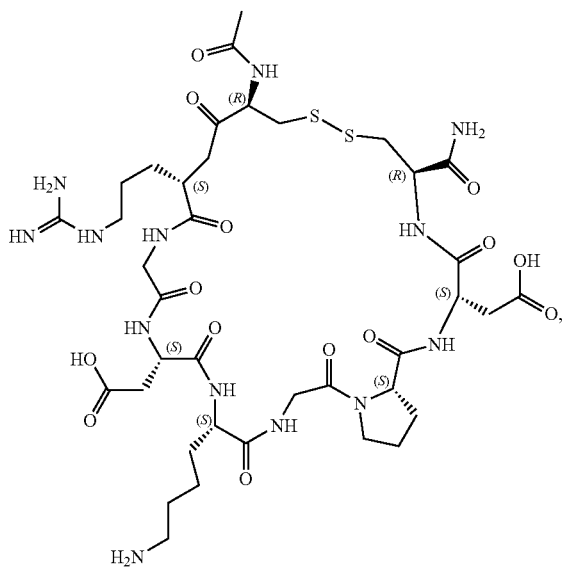

or a pharmaceutically acceptable salt thereof.

2. The cyclic peptide of claim 1, which is in a form of acetate salt.

3. A pharmaceutical composition comprising: the cyclic peptide of claim 1 and a pharmaceutical acceptable excipient.

4. A pharmaceutical composition comprising: the cyclic peptide of claim 2 and a pharmaceutical acceptable excipient.

5. A kit comprising: a therapeutic amount of the cyclic peptide of claim 1, and an anticancer agent.

6. A cyclic peptide with chemical structure as shown below:

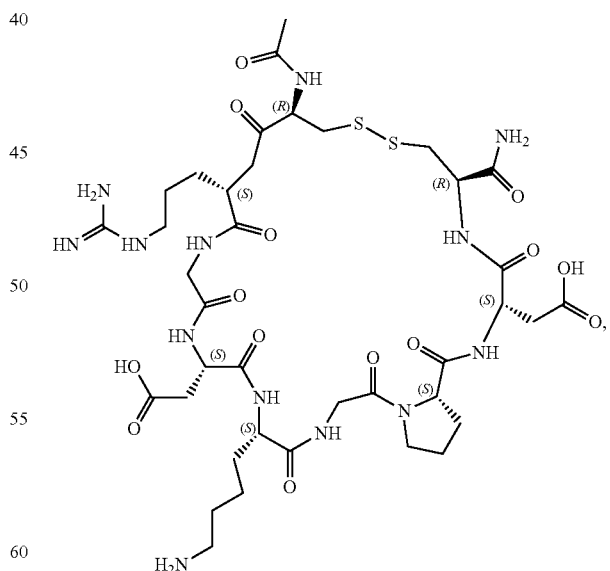

or a pharmaceutically acceptable salt thereof, which is more stable in a phosphate-buffered saline with pH of 7.4 at 37° C. than a reference compound with chemical structure as shown below:

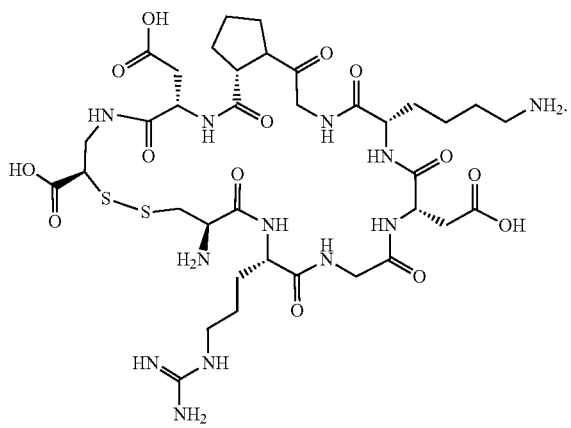 [SMILES: N=C(N)NCCC[C@@H]1NC(=O)[C@@H](N)CSS[C@@H](C(=O)O)CNC(=O)[C@H](CC(=O)O)NC(=O)[C@@H]2CCCC2C(=O)CNC(=O)[C@H](CCCCN)NC(=O)[C@H](CC(=O)O)NC(=O)CNC1=O]

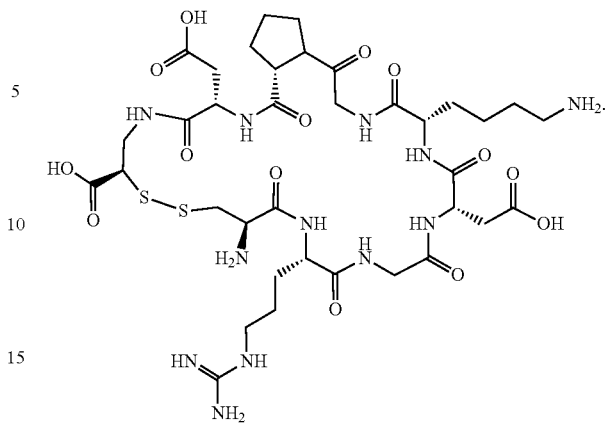

7. The cyclic peptide of claim 6, which is in a form of acetate salt.

8. A pharmaceutical composition comprising: the cyclic peptide of claim 6 which is dissolved in saline, and a pharmaceutical acceptable excipient.

9. A cyclic peptide with chemical structure as shown below:

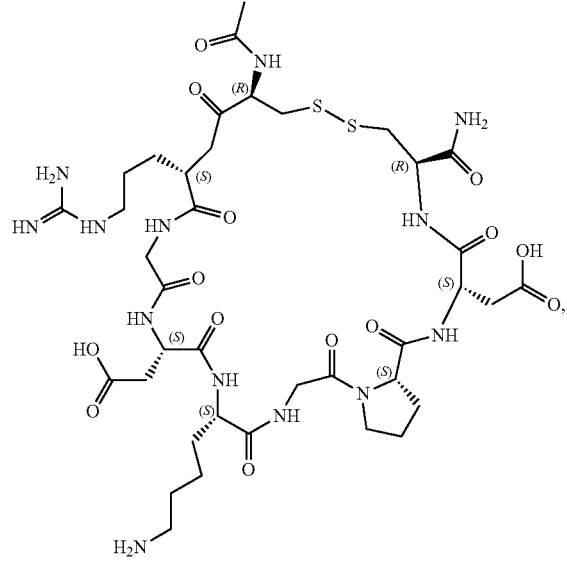

or a pharmaceutically acceptable salt thereof, which is more stable in a pooled human plasma at 37° C. than a reference compound with chemical structure as shown below:

10. The cyclic peptide of claim 9, which is in a form of acetate salt.

11. A pharmaceutical composition comprising: a cyclic peptide with chemical structure as shown below:

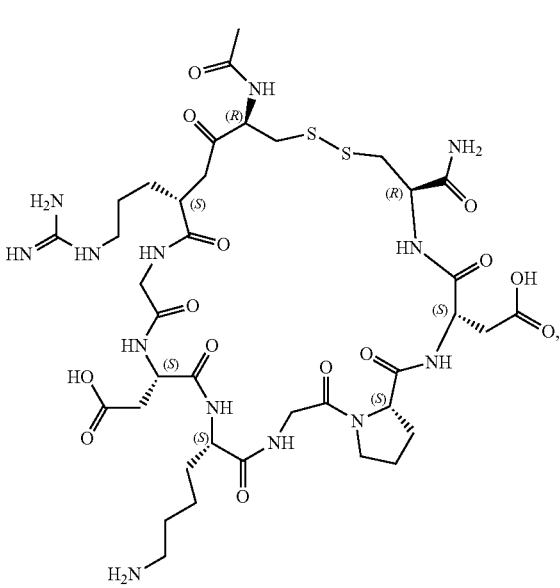

or a pharmaceutically acceptable salt thereof, which is dissolved in saline; and a pharmaceutical acceptable excipient, wherein, at 1 hour of IV administration of a nominal dose of 4.5 mg/kg, the cyclic peptide has a higher mean plasma concentration in mice than a reference compound with chemical structure as shown below with same dose regimen:

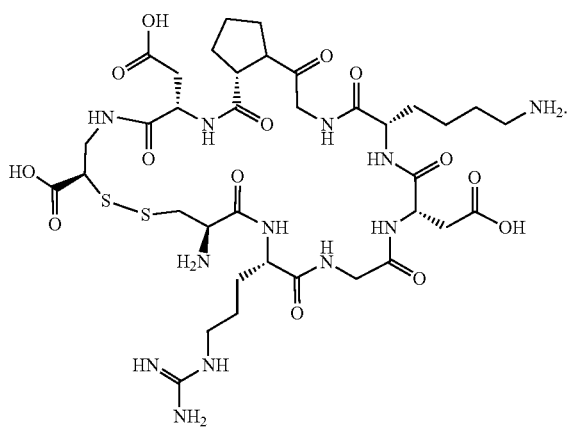 [SMILES: N=C(N)NCCC[C@@H]1NC(=O)[C@@H](N)CSS[C@@H](C(=O)O)CNC(=O)[C@H](CC(=O)O)NC(=O)[C@@H]2CCCC2C(=O)CNC(=O)[C@H](CCCCN)NC(=O)[C@H](CC(=O)O)NC(=O)CNC1=O]

12. The pharmaceutical composition of claim 11, wherein the cyclic peptide is in a form of acetate salt.

13. A pharmaceutical composition comprising: a cyclic peptide with chemical structure as shown below:

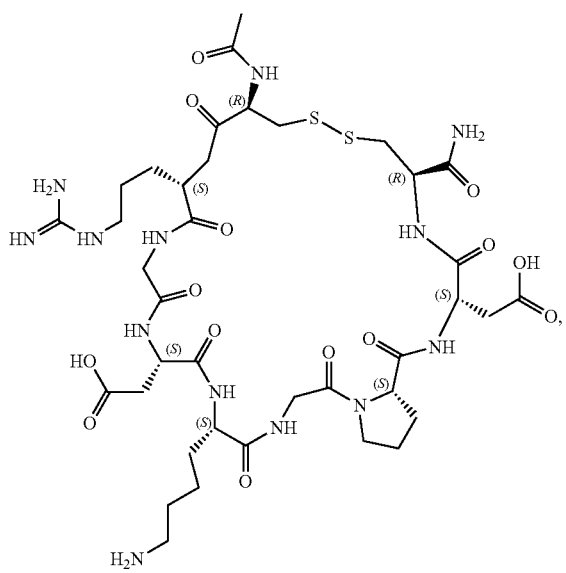

or a pharmaceutically acceptable salt thereof, which is dissolved in saline; and a pharmaceutical acceptable excipient, wherein the cyclic peptide has a longer half-life in mice than that of a reference compound with chemical structure as shown below:

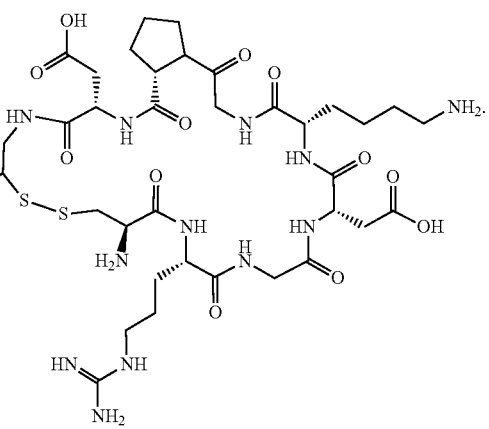

14. The pharmaceutical composition of claim 13, wherein the cyclic peptide is in a form of acetate salt.

\* \* \* \* \*